(12) United States Patent
Hartman et al.

(10) Patent No.: US 6,857,553 B1
(45) Date of Patent: Feb. 22, 2005

(54) METHOD AND APPARATUS FOR IN-PROCESS SENSING OF MANUFACTURING QUALITY

(75) Inventors: Daniel A. Hartman, Santa Fe, NM (US); Vivek R. Dave', Los Alamos, NM (US); Mark J. Cola, Santa Fe, NM (US); Robert W. Carpenter, Los Alamos, NM (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 80 days.

(21) Appl. No.: 10/365,416

(22) Filed: Feb. 13, 2003

Related U.S. Application Data

(60) Provisional application No. 60/373,174, filed on Apr. 17, 2002.

(51) Int. Cl.[7] .......................... B23K 1/00; G01N 29/04
(52) U.S. Cl. ..................... 228/103; 228/104; 73/582; 73/588
(58) Field of Search ............................ 228/103–104, 228/112.1–114.5, 2.1–2.3, 8–9; 73/1.82–1.86, 9, 579, 582, 587, 588, 645, 646

(56) References Cited

U.S. PATENT DOCUMENTS

| | | | | |
|---|---|---|---|---|
| 4,472,971 A | * | 9/1984 | Marini et al. .................. 73/587 |
| 5,283,418 A | * | 2/1994 | Bellows et al. ........ 219/130.01 |
| 5,306,893 A | * | 4/1994 | Morris et al. .......... 219/130.01 |
| 5,448,503 A | * | 9/1995 | Morris et al. .................. 702/66 |
| 5,517,420 A | * | 5/1996 | Kinsman et al. ............. 700/166 |
| 5,652,389 A | * | 7/1997 | Schaps et al. ................. 73/643 |
| 5,659,479 A | * | 8/1997 | Duley et al. ................. 700/166 |
| 5,674,415 A | * | 10/1997 | Leong et al. .......... 219/121.83 |
| 5,882,720 A | * | 3/1999 | Legault et al. .................. 427/8 |
| 6,024,273 A | * | 2/2000 | Ludewig et al. ............. 228/103 |
| 6,308,881 B1 | * | 10/2001 | Hesse et al. ................. 228/102 |
| 2003/0234239 A1 | * | 12/2003 | Lee et al. .................... 219/109 |

FOREIGN PATENT DOCUMENTS

| JP | 10235490 A | * | 9/1998 |
|---|---|---|---|
| JP | 2000046696 A | * | 2/2000 |

OTHER PUBLICATIONS

Translation of JP–2000046696A.*

* cited by examiner

Primary Examiner—Kiley S. Stoner
(74) Attorney, Agent, or Firm—Jim C. Durkis; Dickson G. Kehl; Paul A. Gottlieb

(57) ABSTRACT

A method for determining the quality of an examined weld joint comprising the steps of providing acoustical data from the examined weld joint, and performing a neural network operation on the acoustical data determine the quality of the examined weld joint produced by a friction weld process. The neural network may be trained by the steps of providing acoustical data and observable data from at least one test weld joint, and training the neural network based on the acoustical data and observable data to form a trained neural network so that the trained neural network is capable of determining the quality of a examined weld joint based on acoustical data from the examined weld joint. In addition, an apparatus having a housing, acoustical sensors mounted therein, and means for mounting the housing on a friction weld device so that the acoustical sensors do not contact the weld joint. The apparatus may sample the acoustical data necessary for the neural network to determine the quality of a weld joint.

16 Claims, 17 Drawing Sheets

FIG. 6

| Welding Parameters | | |
|---|---|---|
| Parameter | Setting | |
| Inertial mass | 1.52 | $lbf \cdot ft^2$ |
| Rotational speed | 4500 | $rpm$ |
| Surface velocity* | 589 | $sfpm$ |
| Axial force | 7100 | $lbf$ |
| Weld pressure† | 1092 | $psi$ |
| Weld energy‡ | 5241 | $ft \cdot lbf$ |
| Prebond gap | 0.100 | $in$ |
| Dwell time | 3 | $sec$ |
| Average upset | 0.150 | $in$ |

\* For 0.5 inch diameter bar

† Ram area = 4.9 $in^2$

‡ Energy = $(wk^2 \cdot rpm^2)/5873$

FIG. 7

Variables that were modified during the development of the pattern recognition system

| Module | Possible | Possible Values |
|---|---|---|
| Process Description | microphones | 1<br>1 & 3<br>2 & 4<br>1, 2, 3, & 4 |
| Feature Analysis | window position | 0 – 120,000 |
| Feature Analysis | FFT size | 1024<br>2048<br>4096<br>8192<br>16384 |

FIG. 8

| | Bend test results. | | |
|---|---|---|---|
| Weld Number | Surface Condition Before Welding | Bond Quality | Bonded Area (%) |
| 1 - 12 | Freshly Machined | Acceptable | 100.0 |
| 13 | Freshly Machined | Conditional | 80.0 |
| 14 | Freshly Machined | Conditional | 70.0 |
| 15 | Freshly Machined | Conditional | 69.0 |
| 16 | Freshly Machined | Conditional | 67.0 |
| 17 | Freshly Machined | Conditional | 54.0 |
| 18 | Freshly Machined | Conditional | 26.0 |
| 19-23 | Not Machined | Unacceptable | 0.0 |

Acceptable 902   906   904

Conditional

902'   906'   904'

Unacceptable

902"   906"   904"

910   912   916   914

910'   912'   916'   918'   920'   914'

910"   918"   920"   914"

US 6,857,553 B1

METHOD AND APPARATUS FOR IN-PROCESS SENSING OF MANUFACTURING QUALITY

CROSS-REFERENCE TO RELATED APPLICATIONS

This application claims the priority of the co-pending U.S. Provisional Patent Application No. 60/373,174, entitled "Method and Apparatus for In-Process Sensing of Manufacturing Quality," filed Apr. 17, 2002. The entire disclosure and contents of the above application is hereby incorporated by reference.

GOVERNMENT INTEREST STATEMENT

The United States Government has rights in this invention pursuant to Contract No. W-7405-ENG-36 between the United States Department of Energy and the University of California for the management and operation of the Los Alamos National Laboratory.

BACKGROUND OF THE INVENTION

1. Field of the Invention

The present invention relates to methods for sensing the quality of a weld joint.

2. Description of the Prior Art

Traditionally, critical inertia-friction welded joints tend to be difficult to inspect for two reasons: (1) non-destructive evaluation techniques only detect gross disbonds leaving more subtle discontinuities which could have a significant effect on fatigue life or joint fracture toughness; and (2) destructive post-process inspection is time-consuming and costly for highly man-rated or labor intensive applications.

Although improvements in post-process, nondestructive tests have been realized in research and development laboratory environments, such as described in Armstrong, B., *Ultrasonic Analysis of Inertia Friction Welds Between Similar and Dissimilar Alloys*, M.S. thesis, The Ohio State University, Department of Welding Engineering (1986), the entire contents of which are hereby incorporated by reference, no reliable method is available for detecting in-situ weld quality in a production environment. For commercial applications, weld parameter development and post-process inspection efforts can result in up to a 200%-time (and cost) overhead in the overall manufacturing process with little value added. Therefore, there exists a need for a commercially feasible apparatus and method using an in-process means of determining part quality of a weld joint to reduce costs and increase quality.

SUMMARY OF THE INVENTION

It is therefore an object of the present invention to provide a method and apparatus that will provide a nondestructive inspection means of a weld joint formed by a friction weld process.

It is a further object to provide an apparatus having noncontact acoustical sensors for sampling an acoustical signature.

It is yet another object to provide a method and apparatus for identifying features in an acoustical signature from a weld joint that correlates to weld quality.

It is yet another object to provide a method and apparatus for correlating features in an acoustical signature from a weld joint to categories of weld quality using a neural network.

It is yet another object to provide a method and apparatus for distinguishing between types of categories of weld quality such as acceptable, conditional and unacceptable.

It is yet another object to provide a method for training a neural network so that a trained neural network may determine the quality of weld joint, using both destructively observed weld joints or test weld joints and nondestructively observed weld joints or examined weld joints.

It is yet another object to provide a method and apparatus for reducing the cost and time involved in post friction weld process inspection of a weld joint.

It is yet another object- to provide a method and apparatus for performing the nondestructive inspection of a weld joint in real time.

Finally, it is an object of the invention to provide a method and apparatus for determining the quality of a weld joint based on the result of a neural network.

According to a first broad aspect of the present invention, there is provided a method for determining the quality of an examined weld joint comprising the steps of (a) providing acoustical data from the examined weld joint, and (b) performing neural network operations on the acoustical data to determine the quality of the examined weld joint, wherein the examined weld joint is produced by a friction weld process.

According to second broad aspect of the invention, there is provided a method for training a neural network comprising the steps of (a) inputting acoustical data from at least one test weld joint, (b) inputting observable data from at least one test weld joint, and (c) training the neural network based on acoustical data and observable data from at least one test weld joint to form a trained neural network so that the trained neural network is capable of determining the quality of a examined weld joint based on acoustical data from the examined weld joint.

According to third broad aspect of the invention, there is provided an apparatus comprising a housing, at least one acoustical sensor mounted in the housing, and housing mounting means for mounting the housing on a friction weld apparatus so that that at least one acoustical sensor can sample an acoustical signature from a weld joint.

Other objects and features of the present invention will be apparent from the following detailed description of the preferred embodiment.

BRIEF DESCRIPTION OF THE DRAWINGS

The invention will be described in conjunction with the accompanying drawings, in which:

FIG. 6 is a table that shows weld parameters used in example one of the invention;

FIG. 7 is a table that shows variables that were modified during the development pattern recognition system in example one of the invention;

FIG. 8 is a table that shows bend test results in example one of the invention;

DETAILED DESCRIPTION OF THE PREFERRED EMBODIMENT

It is advantageous to define several terms before describing the invention. It should be appreciated that the following definitions are used throughout this application.

DEFINITIONS

Where the definition of terms departs from the commonly used meaning of the term, Applicants intend to utilize the definitions provided below, unless specifically indicated.

For the purposes of the present invention, the term "quality" refers to the characteristics of a weld joint, such as exhibiting high or good tensile strength and weld ductility, that are indicative of the weldability of the materials. For example, a quality weld joint may exhibit a strong welded connection between the materials. Quality may be visually determined by the percentage of the surface area of the interfaces of the two materials that exhibit bonding as a result of a friction weld process. Quality may be important in determining the durability of a weld joint, which may experience various levels of stress when the weld joint is applied in various applications.

Figure 9A:
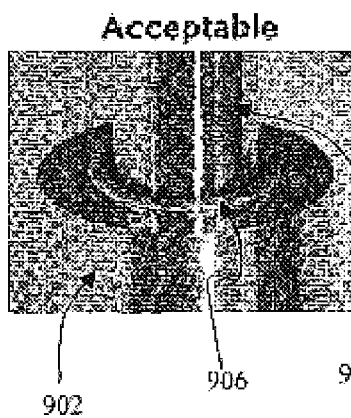
FIG. 9A is a picture showing a perspective view of a copper-stainless steel weld joint having an acceptable result used in example one of the invention.
Figure 9B:
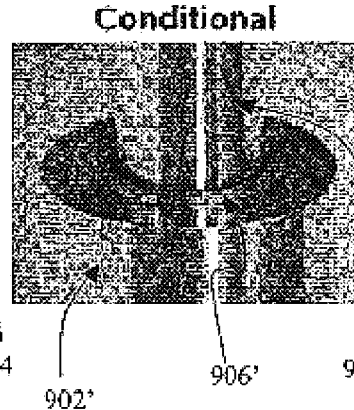
FIG. 9B is a picture showing a perspective view of a copper-stainless steel weld joint having a conditional result used in example one of the invention.
Figure 9C:
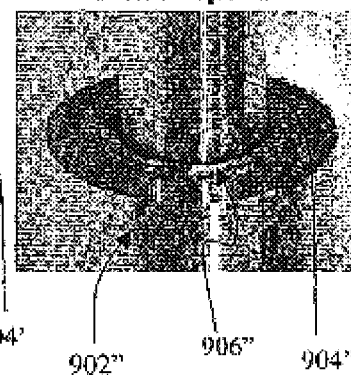
FIG. 9C is a picture showing a perspective view of a copper-stainless steel weld joint having an unacceptable result used in example one of the invention.

For the purposes of the present invention, the term "weld joint" refers to the point of contact or interface between two materials that are welded using a friction welding process. The weld joint may be formed when both work-piece materials' interfaces are consolidated under pressure produced by a friction weld. Examples of weld joints are shown in FIGS. 9A–9C. For the purposes of the present invention, the term weld joint may refer to an examined weld joint or a tested weld joint.

For the purposes of the present invention, the term "examined weld joint" refers to a weld that will be examined to determine weld quality, without destructively testing the weld joint to determine the weld quality. The acoustical data from an examined weld joint may be used to further train a neural network.

For the purposes of the present invention, the term "tested weld joint" refers to a weld joint that is destructively tested to determine by observing the weld quality of a weld joint. The observed and acoustical data from a tested weld joint may be used in the method of the present invention to train a neural network.

For the purposes of the present invention, the term "destructively tested" refers to any method where the weld joint breaks apart to allow one to observe the bond between the work piece materials. Destructively tested may be performed by a machine or human.

For the purposes of the present invention, a value, data, signal, or other factor is "dependent" or "based" on a particular value, property, the satisfaction of a condition, or other factor, if that value, data, signal, or other factor is derived by performing a mathematical calculation or logical decision using that value, data, signal, or other factor. For example, a processed signal may be based on a signal that has been processed by being filtered, transformed and normalized using various mathematical operations or formulas. Also, an output may be based on a signal that has been processed using frequency information from an acoustical signature using a discrete Fourier transform and using phase information derived from the time-domain relationship from each microphone in a sensor.

For the purposes of the present invention, the term "acoustical data" refers to raw data in acoustical signature that may be preprocessed, extracted, etc. The acoustical data may be used as a input for the neural network, after the raw data has been preprocessed. The acoustical data may be represented by at least one signal. For example, while measuring the acoustical signature or emission from a friction weld joint, the acoustical sensors may be able to determine a raw data point such as amplitude. Before including the raw data or amplitude in the neural network, the raw data must be preprocessed, or extracted to form acoustical data, such as, in this case, frequency. Preferably, acoustical data is included into a neural network when training or testing the neural network.

Figure 9D:
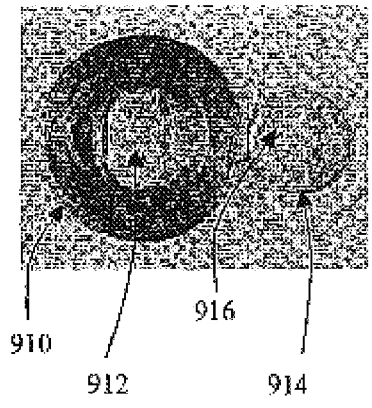
FIG. 9D is a picture showing a top view of FIG. 9A having a fracture surface for an acceptable bond quantity in example one of the invention.
Figure 9E:
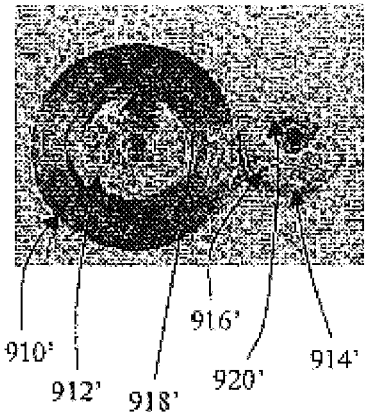
FIG. 9E is a picture showing a top view of FIG. 9B having a fracture surface for a conditional bond quantity in example one of the invention.
Figure 9F:
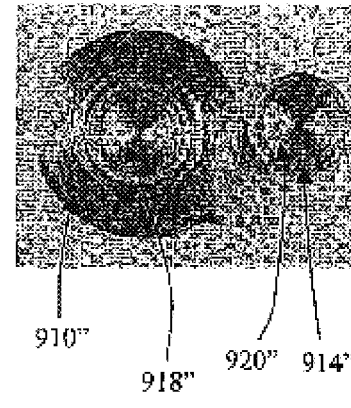
FIG. 9F is a picture showing a top view of FIG. 9C having a fracture surface for an unacceptable bond quantity in example one of the invention.

For the purposes of the present invention, the term "observed data" refers to data that is observed through visual inspection. The observation of observed data may be made with the assistance of a microscope, to determine the bonded areas produced by a weld joint. Observed data may be obtained from the destructive testing of a test weld joint. The observed data may be used to train a neural network so that a trained network does not have to use observed data to determine the quality of a weld joint from an examined weld joint. For example, FIGS. 9D–9F show fractured weld joints that have observable data that can be inputted into a neural network.

For the purposes of the present invention, the term "neural network" refers to a structure of the information processing system having several interconnected layers, which simulates a biological neuron pattern. A neural network may be composed of a large number of highly interconnected processing elements that are analogous to neurons and may be tied together with weighted connections that are analogous to synapses. A neural network may refer to an artificial neural network (ANN) or probabilistic neural network (PNN). The development of PNN is described in Specht, D., "Probabilistic Neural Networks for Classification, Mapping or Associative Memory," in *Proceedings of the IEEE International Conference on Neural Networks*, 1988, vol. 1, pp. 525–532, and Specht, D., *Neural Networks*, 3, 109–118 (1990), the entire contents and disclosure of which are hereby incorporated by reference. Preferably, a neural network operates by training, wherein the training adjusts to the exposure known true values for an input/output. A neural network may be well suited to handling data sets where the structure is ill-defined and which contains both deterministic and random signals. A neural network may refer to a supervised neural network or an unsupervised neural network.

For the purposes of the present invention, the term "performing neural network operations," refers to an operation on data performed by a neural network. For example, performing a neural network operation may require inputting or providing data to the neural network and performing a series of operations of the neural network to produce an output. The type of neural network used to analyze data may define the operations performed by a neural network.

For the purposes of the present invention, the term "acoustical signature" refers to the raw data that is gathered from a weld joint during or after the stages of a friction weld process. The acoustical signature may be represented by at least one signal. The acoustical signature may also be referred to as the acoustical emission (AE). The acoustical signature may include acoustical energy, sound pressure, amplitude, mechanical properties and phenomenon, thermal properties and phenomenon, metallurgical properties and phenomenon, etc. For example, the acoustical signature may contain frequency information and phase information when multiple acoustical sensors are used. Preferably, an acoustical signature is sampled using acoustical sensors and processed to obtain acoustical data suitable for inclusion into training the neural network for determining the quality of an examined weld joint.

Figure 11A:
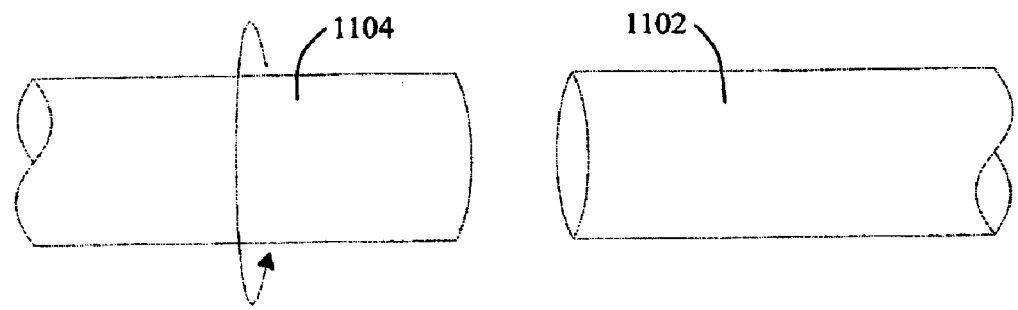
FIG. 11A is a schematic representation of stage one of a friction weld process in accordance with a preferred embodiment of the present invention.
Figure 11B:
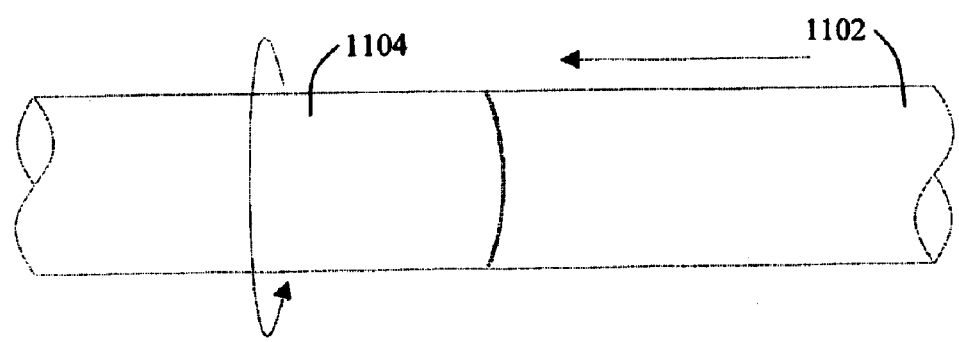
FIG. 11B is a schematic representation of stage two of a friction weld process in accordance with a preferred embodiment of the present invention.
Figure 11C:
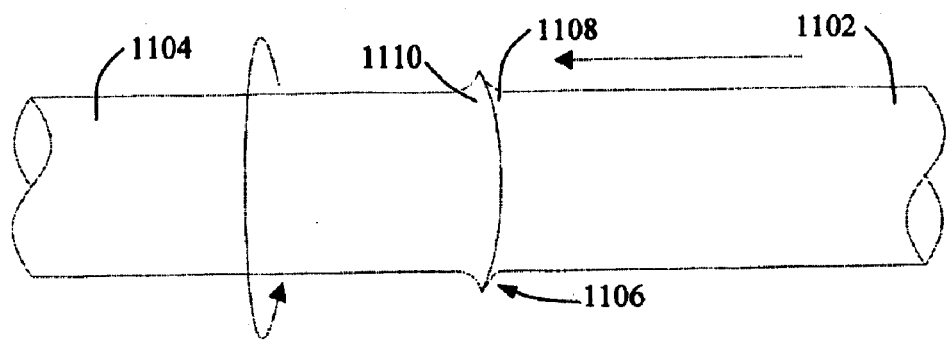
FIG. 11C is a schematic representation of stage three of a friction weld process in accordance with a preferred embodiment of the present invention.
Figure 11D:
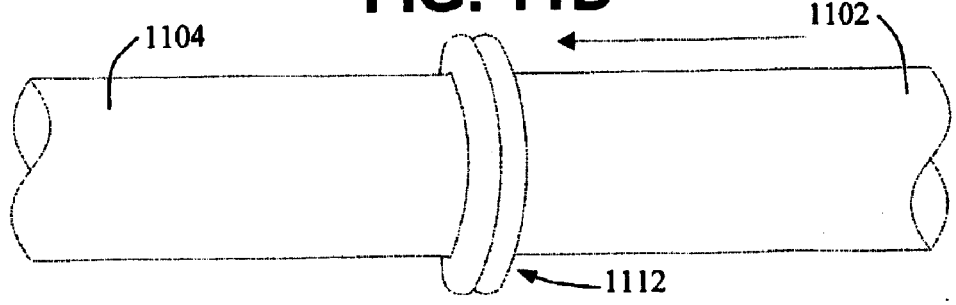
FIG. 11D is a schematic representation of stage four of a friction weld process in accordance with a preferred embodiment of the present invention.
Figure 12:
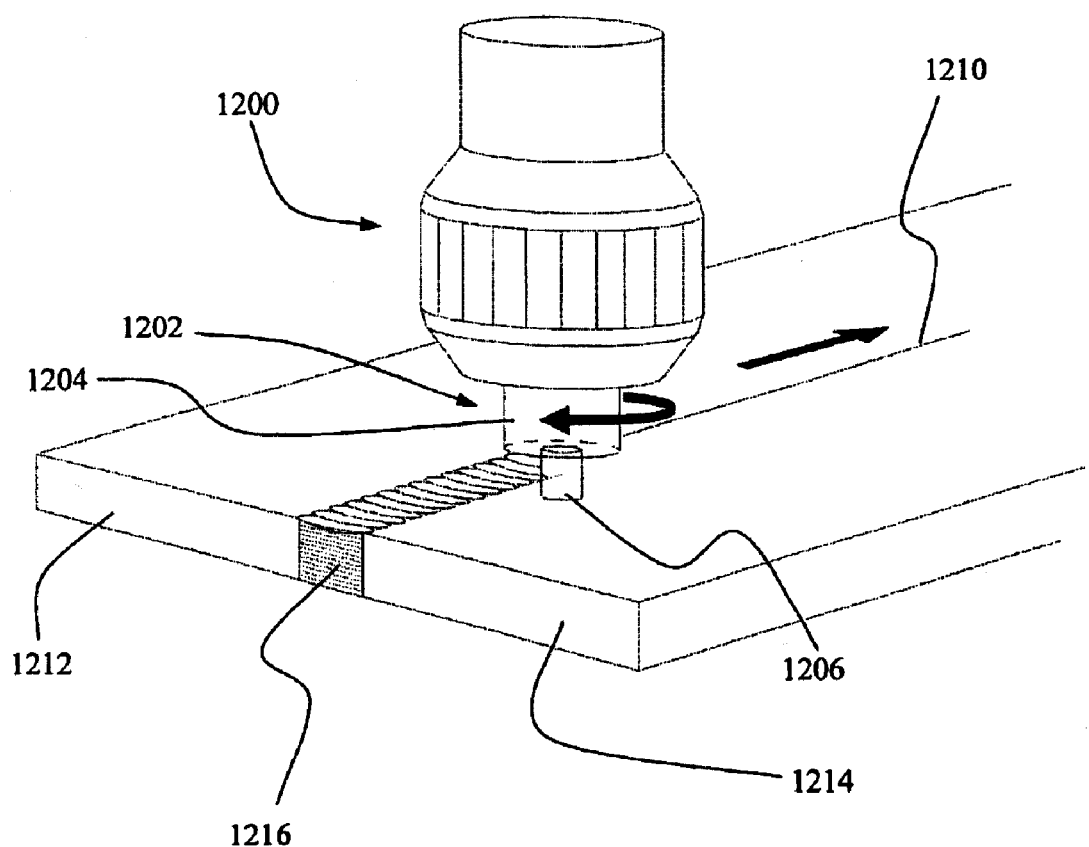
FIG. 12 is a perceptive view of a friction stir weld process in accordance with a preferred embodiment of the present invention.

For the purposes of the present invention, the term "friction welding" or "friction weld process" refers to any conventional friction welding of two materials wherein heat is generated at the interface of the two materials and pressure is used to consolidate the two materials together. A friction weld process may involve welding two dissimilar metals together, such as ferrous and non-ferrous metals. A typical friction weld process may involve the following stages, as shown in FIGS. 11A–11D. In the first stage, one of the two work-piece materials is rotated at a predetermined speed, while the other work-piece material is held stationary. In the second stage, the two work-pieces are brought together under compression and an axial force is applied. The duration of the rotation is a function of the nature of the materials and size. In the third stage, the compressive and frictional forces produce heat causing the displacement of material, referred to as flash, at the faying surfaces. In the fourth stage, rotation stops and axial force is maintained for a predetermined amount of time to complete the weld. It should be appreciated that other friction weld processes may be used. Friction welding process includes direct or continuous friction welding, hybrid friction welding, solid-state welding, inertia friction welding, friction stir welding as shown in FIG. 12, friction hydropillar processing, and friction surfacing etc. Friction welding processes do not include methods that utilize arc welding techniques that uses the heat generated by the tip of an electrode and filler metal to produce a weld joint.

For the purposes of the present invention, the term "acceptable" refers to classification category for welds that have a majority or substantially all of the interfacing surfaces bonded. For example, FIG. 9D that shows an unacceptable weld. An acceptable result may be indicated by a light, LED, sound, sequence of events, pulse, visual indication, graphically, numerically, etc. when a trained neural network based on acoustical data from an examined weld joint shows that the weld is acceptable. Preferably, the acceptable indicator has a different orientation than the other categories of conditional or unacceptable.

For the purposes of the present invention, the term "conditional" refers to classification category for welds that have most or some of the interfacing surfaces bonded. For example, FIG. 9E that shows an unacceptable weld. A conditional result may be indicated by a quality determining apparatus having a light, LED, sound, sequence of events, pulse, visual indication, graphically, numerically, etc. when a trained neural network based on acoustical data from an examined weld joint shows that the weld is conditional. Preferably, the conditional indicator has a different orientation than the other categories of acceptable or unacceptable.

For the purposes of the present invention, the term "unacceptable" refers to classification category for welds that have no or little bonding at the surface. For example, FIG. 9F that shows an unacceptable weld. An unacceptable result may be indicated by a quality determining apparatus having a light, LED, sound, sequence of events, pulse, visual indication, graphically, numerically, etc. when a trained neural network based on acoustical data from an examined weld joint shows that the weld is unacceptable. Preferably, the conditional indicator has a different orientation than the other categories of acceptable or conditional.

For the purposes of the present invention, the term "computer" refers to any type of apparatus having a means for storing and processing data. Computers include personal computers, mainframe computer, mini-computer, etc. or an intranet or a worldwide network of computers, such as a network of computers in a business, etc. For example, a computer may perform the calculations necessary for the neural network to be trained.

For the purposes of the present invention, the term "quality determining apparatus" refers to any device, such as a computer, that informs a user of the quality of a weld joint.

DESCRIPTION

Previous research into in-process quality detection of friction welds is described in Wang, K., Reif, G., and Oh, S., "In-Process Quality Detection of Friction Welds Using Acoustic Emission Techniques," *Welding Journal*, 61, 312s–316s (September 1982), the entire contents are hereby incorporated by reference. This research demonstrated the feasibility of using acoustical emission (AE) as an in-process quality metric for inertia friction welding (IFRW) of ferrous metals. This research was able to correlate AE counts to joint strength for bar-to-bar (AISI 4140 to 1117 and 12L14) and tube-to-tube (AISI 1020 to 304SS) welds. AE sensing was accomplished with a piezoelectric transducer attached directly to either the stationary chuck or the work piece. For mild steels, this research found two distinctive regions of AE: one during the welding process (A-zone) and the other during the cool-down portion of the weld cycle (B-zone). The first burst of AE activity is due primarily to the plastic deformation of the material during the weld, whereas the second burst of AE activity is suspected to be a result of martensitic transformation. This research showed relatively good correlation between the cumulative B-zone AE counts and the tensile breaking force, i.e., strength, for ferrous metals. However, non-ferrous metal experiments, such as aluminum and copper, resulted in no detectable B-zone AE activities, and hence this research was unable to determine weld strength.

An extended analysis on the previous research is described in Oh, S., A., H., Kunio, T., and Wang, K., *Transactions of the Japan Welding Society*, 13, 15–26 (1982), and Oh, S., Oh, J., Jeon, T., and Oh, S., "Development of Real-Time Quality Evaluation of Friction Welding by Acoustic Emission: Report 1," in *Proceedings of the Fifth International Offshore and Polar Engineering Conference*, The International Society of Offshore and Polar Engineers, The Hague, The Netherlands, 1995, vol. 4, pp. 163–168, the entire contents of these documents are hereby incorporated by reference. This research used the total cumulative AE counts, i.e., A-zone counts+B-zone counts, as an in-process quality metric. In particular, this research was able to correlate weld strength with (1) total cumulative AE counts and initial energy, (2) total cumulative AE counts and total upset, and (3) total cumulative AE counts and welding time, for continuous drive friction welding. This research was able to empirically derive an equation for tensile strength that can be used for in-process monitoring and control of friction weld strength. Other research as described in Oh, S., Oh, J., and Chang, H., "Development of Real-Time Quality Evaluation of Friction Welding by Acoustic Emission: 2nd Report. Effects of Welding Parameters on Weld Strength and AE," in *Proceedings of the Sixth International Offshore and Polar Engineering Conference*, The International Society of Offshore and Polar Engineers, Los Angeles, Calif., USA, 1996, vol. 4, pp. 177–184, the entire contents are hereby incorporated by reference, correlated weld strength to IFRW welding parameters, such as rotational speed, pressure, and inertia, and total cumulative AE counts. The final report of this research that correlates Zone-A AE counts and weld strength is described in Oh, S., Park, H., and Lee, B., "Development of Real-Time Quality Evaluation of Friction Welding by Acoustic Emission: 3rd Report. Effects of Initial AE Counts During Plastic Deformation in FRW," in *Proceedings of the Seventh International Offshore and Polar Engineering Conference*, The International Society of Offshore and Polar Engineers, Honolulu, Hi., USA, 1997, vol. 4, pp. 535–540, the entire contents and disclosure of which is hereby incorporated by reference.

The current industry approach to ensuring quality in IFRW relies upon maintaining absolute upset within a predetermined ±3 σ envelope and applies this quality metric post-process. Previous work as described by Hartman, D., Cola, M., and Dave, V., "Eliminating Post-Process Inspection of Inertia Friction Welds Through In-Process, Quality-Based Monitoring," in *82nd Annual AWS Convention, Abstracts of Papers*, Cleveland, Ohio, 2001, pp. 190–192, the entire contents and disclosure is hereby incorporated by reference demonstrated that this technique is capable of detecting faulty welds when machine parameters varied slightly from their nominal. However, other defect conditions, such as, surface contamination and misalignment, were not detectable by monitoring absolute upset.

Other methods may use acoustical sensors to determine the quality of a weld joint, but these methods are not suited for a friction weld process. Previous methods are described in U.S. Pat. No. 6,018,729 to Zacharia, et al., and U.S. Pat. No. 5,448,503 to Morris, et al., the entire contents of which are hereby incorporated by reference. Such methods may train neural networks based on the data from acoustical sensors but only apply arc-welding techniques. These methods cannot be applied to a non-contact or nondestructive inspection of a weld joint produced by a friction weld process.

The present invention overcomes the shortcomings of the prior research and art by using a novel, noncontact, nondestructive acoustical sensing technique and method using an apparatus for acoustical sensing. The present invention may be used to sense the acoustical signature of a weld joint during welding or after the friction welding process is complete. Preferably, the present invention may be used to determine or sense the quality of a weld joint in real time during a friction welding process. In particular, the acoustical data sampled from the acoustical sensors may be analyzed using a neural network pattern classification system in order to determine that information, such as frequency or phase information, exists within the acoustical data that may be correlated to weld characteristics, such as bond quality. Further, the present invention provides a method determining the weld quality of weld joint once a neural network is trained, so that acoustical data may be correlated to a quality metric, such as, acceptable, unacceptable, or conditional.

In one preferred embodiment of the present invention, there is provided a method for determining the quality of an examined weld joint comprising the following steps of providing or inputting acoustical data from the examined weld joint, and performing neural network operations on the acoustical data to determine the quality of the examined weld joint, wherein the examined weld joint is produced by a friction weld process. Preferably, the method of the first embodiment is performed in real-time while the examined weld joint is formed from the friction weld process. Alternatively, the method of the first embodiment may be performed during all stages of the friction weld process, and acoustical data from all stages may be used as inputs to a pattern classification system to determine weld quality in-situ.

The present invention may classify types of welds based on the quality of the weld joint. A preferred type of classification may include defining an acceptable weld and unacceptable weld. An acceptable weld may be a weld joint in which the majority of the interfacing surfaces are bonded. An unacceptable weld may be a weld joint in which no or little bonding at the surfaces exists. In addition, a third classification may include defining conditional weld in which the weld joint is between the acceptable and unacceptable classification. The classifications may be combined in a number of ways, such as acceptable/unacceptable, acceptable/conditional, conditional/unacceptable, and/or acceptable/conditional/unacceptable.

The classifications may also involve a first classification of acceptable/unacceptable and a second classification of acceptable/conditional or vice versa. This arrangement of determining quality of weld joint by using to sets having one common category allows a classification of a weld joint based on all three categories of acceptable/conditional/ unacceptable. This arrangement is more preferable because the neural network produces a binary output suitable to a two-step classification process.

Preferably a neural network, such as an PNN, may be used to analyze the acoustical data and observed data sampled from a tested weld joint to train the neural network so that the neural network may determine the quality of a weld joint based on acoustical data from an examined weld joint. The process of a neural network is described in more detail in following paragraphs and elsewhere through the specification.

A neural network may be trained using a fix set of tested weld joints and the parameters of a quality weld joint is set for future use of examined weld joints. The method training a neural network based on a fixed set of tested weld joints comprises the following steps of inputting acoustical data from at least one test weld joint, inputting observable data from the same at least one test weld joint, and training the neural network based on acoustical observable data to form a trained neural network so that the trained neural network is capable of determining the quality of an examined weld joint based on acoustical data from the examined weld joint. The neural network may use as many test weld joints as necessary to meet the parameters for quality. Preferably, the neural network may use 5–50,000 test weld joints. More preferably, the neural network may use 10–1,000 test weld joints. Most preferably, the neural network may use 20–100 test weld joints. In commercial applications, the fewer number of weld joints may be sufficient to train a neural network. However, in large commercial applications may require a high number of test weld joints when a particular level of quality is necessary to ensure the weld joint performs under its operating conditions. Additional, more test weld joints may be included to further train a neural network that has already been trained by a previous set of test weld joints. Once a model has been developed or trained, the neural network or other pattern classification technique may evolve throughout the manufacturing process by incorporating new training instances and adapting, or refining, its classification strategies appropriately.

Alternatively, a neural network may be trained using an adjusted set of tested weld joints and possibly using a first examined weld joint to determine the quality of a second examined weld joint. This alternative may allow a neural network to become adaptive to set of quality conditions that may fluctuate over time depending on the user's requirements for the quality standard of a weld joint. The method of training a neural network based on an adaptation may involve first training the neural network on a fixed set of test weld joints as described by the previous paragraph. Preferably, training a neural network on a fixed set of test weld joints is advantageous for establishing primitive quality parameters. However, a neural network may be trained entirely on the adaptation method using solely examined weld joints. When the neural network is first trained on a fixed set of tested weld joints, the method further comprises inputting acoustical data from a first examined weld joint, and training the neural network based on the acoustical data to form a trained neural network so that the trained neural network is capable of determining the quality of a second examined weld joint based on acoustical data from the second examined weld joint.

As described above, the neural network may receive inputs of acoustical data and observation data when analyzing the quality of a weld joint. The acoustical data may be sampled from the acoustical emissions or acoustical signature of a weld joint. Preferably, an acoustical sensor may be used to sample the acoustical signature. More preferably, an acoustical sensor comprised of a housing, at least one acoustical sensor mounted in the housing, and a means for mounting the housing on the friction weld device may be used to sample the acoustical signature. The acoustical sensor may be microphone. Preferably, four microphones may be used as acoustical sensors to sample the acoustical signature. Alternative, the acoustical sensor may comprise a plurality of microphones from one to twelve. The acoustical sensor may sample the acoustical signature at 40 kHz. Preferably, the acoustical sensors are mounted at an equal distance from the weld joint. The housing may be in any shape, such as a circle, rectangle, octagon, ellipse, horseshoe, etc. The housing and means for mounting the housing may be made of any material, such as a metal or metal alloy, plastic, composite material, etc.

The acoustical data may be based on raw data from the acoustical signature. The raw data may comprise time domain data and/or frequency information, such as the amplitude of the acoustical signature. The acoustical data may be based on frequency information. Preferably, prior to basing the acoustical data on the frequency information, a moving window discrete Fourier transform (DFT) was preformed on the raw data from the acoustical signature using the fast Fourier transform (FFT) algorithm.

When at least two microphones are used to sample the acoustical signature, raw data may also include phase information. The acoustical data may be based on frequency information and phase information. Preferably, phase information is based on a time-domain relationship between the at least two microphones. When sampling the acoustical signature for 3 seconds at 40 kHz, using four microphones, 160,000 data points would be obtained. Other numbers of data points are possible using different combinations of microphones and time intervals. A step size of 250 data points may be used to reduce the time and complexity in calculating the acoustical data. Other step sizes of 100–1000 are possible and may be used when analyzing the raw data from an acoustical signature.

Each segment of the time-domain from the raw data of the acoustical signature may be filtered using a Hanning Window to form filtered data. The filtered data may be transformed into the frequency domain to form transformed data. The transformed data may be normalized before the acoustical data is ready to be included as an input for the neural network. When at least two microphones are used to sample the acoustical signature, the normalized transformed data from a first microphone may be appended to a second microphone to form appended data prior to including the appended data as acoustical data for the neural network. A first microphone would sample a first acoustical signature. The first acoustical signature would be filtered using the Hanning window to form a first filtered data. The first filtered data may be transformed to form a first transformed data. The first transformed data may be normalized. A second microphone would sample a second acoustical signature. The second acoustical signature would be filtered to form a second filtered data. The second data signal may be transformed to form a second transformed data. The second transformed data may be normalized. The first normalized transformed data and the second transformed data may be appended together to form appended data. A preferred method for the present invention may be to use at least four microphones when sampling the acoustical signature. The raw data from the acoustical signature sampled by the four microphones may then be appended together as described above, with the additional steps for the third and fourth microphone Once the neural network analyzes the inputs for a test weld joint and/or an examined weld joint and the neural network determines that a weld joint has a particular quality, such as acceptable, conditional, or unacceptable, the neural network may trigger an indicator to represent the quality of the weld joint analyzed. The indicator may be a LED, light, bleep, sound, pulse, output to a computer screen, etc. For example, the neural network would determine that a weld quality is either acceptable or unacceptable. An output of 1 may represent the acceptable quality, while an output of 0 may represent the unacceptable quality. This output may cause a green LED to illuminate on a quality determining apparatus, such as a computer, so that the user may recognize the quality of the weld joint as being acceptable. Illuminating a red LED may show an unacceptable quality. Alternatively, a chart may be created as an indicator using a quality determining apparatus to show the classification accuracy versus time to be used to determine the quality of a weld joint. The features within an acoustical signature may be identified to infer quality of the weld joint as indicated by the chart.

The neural network process may be implemented or performed by a computer. The computer may process the inputs into the neural network and using the training pattern or learning process of the neural produce a binary output.

In another preferred embodiment of the present invention, there is provided a method for training a neural network comprising the steps of inputting or providing acoustical data and observable data from at least one test weld joint, and training the neural network based on the acoustical data and the observable data to form a trained neural network. The trained neural network is capable of determining the quality of an examined weld joint based on acoustical data from the examined weld joint. The method for training a neural network may use a series of training patterns that may consist of sets of acoustical data and/or observable data. A neural network may be trained prior to determining the quality of an examined weld joint or a neural network may be trained while determining the quality of an examined weld joint.

A neural network may be trained using at least one test weld joint. Preferably, a neural network may be trained using a plurality of test weld joints, as described above. In additional, the training of a neural network may be examined weld joints when the training is to be performed continuously or is an adaptive to additional examined weld joints.

When the neural network is being trained, the neural network may be capable of determining whether the examined weld joint is acceptable or conditional. Additionally, the neural network may be capable of determining whether the examined weld joint is acceptable or unacceptable. The test weld joint is known to be either acceptable, conditional, or unacceptable based on the observable data.

In another preferred embodiment of the present invention, there is provided an apparatus comprising a housing, at least one acoustical sensors mounted in the housing, a means for mounting at least one acoustical sensor, wherein the housing includes means for mounting the housing on a friction weld apparatus so that that at least one acoustical sensor can sample an acoustical signature from a weld joint. The mounting of the apparatus on the friction weld apparatus may allow at least one acoustical sensor to sample an acoustical signature that may be used to trained a neural network to determine the quality of a weld joint.

Preferably, the housing may be mounted on the friction weld device so that the acoustical sensor or sensors do not touch or contact the weld joint. Alternatively, the apparatus of the present invention may be mounted on another means, such as the floor or ceiling, so long as the acoustical sensors do not contact the weld joint. The present invention may have any number of acoustical sensors mounted in the housing. Preferably, at least 1 to 12 acoustical sensors are mounted in the housing. Preferably, the acoustical sensors are microphones.

When at least two acoustical sensors are mounted in a housing, the acoustical sensors may be a substantially equal distance from the weld joint. Preferably, the acoustical sensors may be at least 0.1 cm to 20 cm in distance from the weld joint. More preferably, the acoustical sensor may be at least 1 cm to 10 cm in distance from the weld joint. Most preferably, the acoustical sensor may be at least 2 cm to 4 cm in distance from the weld joint. The distance may be in any plane or direction. In addition to the distance from the weld joint, the acoustical sensors may be spaced in the housing at an equal distance from each other.

Figure 1:
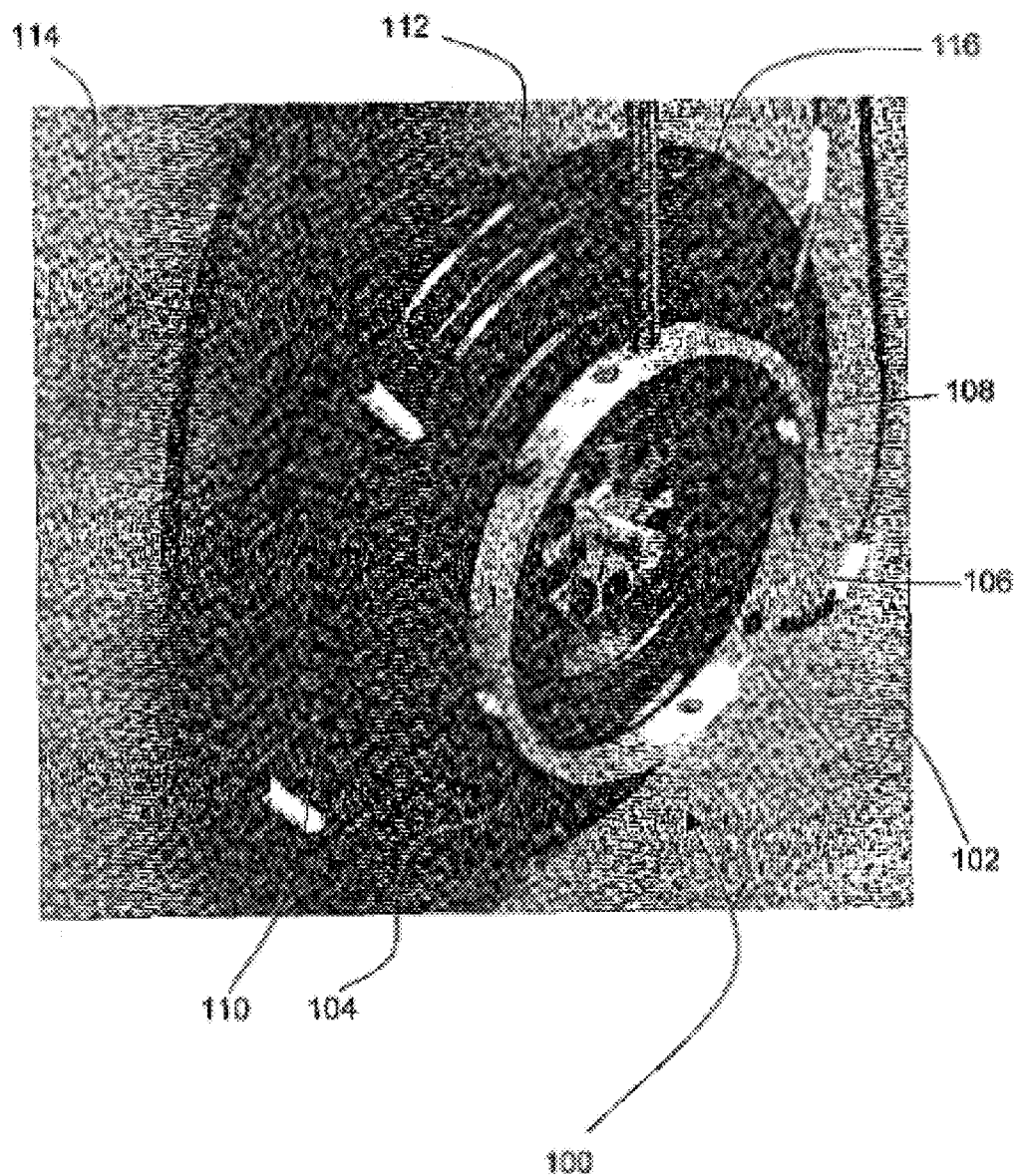
FIG. 1 is a photograph having a perspective view of a housing with mounted sensors mounted on a friction weld device constructed in accordance with a preferred embodiment of the invention.

FIG. 1 shows a preferred embodiment of the present invention including an acoustical sensing apparatus 100 that consists of an acoustical sensor 102 that is mounted in a housing 104, which surrounds a work piece material 106 in a segmented collet 108. Acoustical sensor 102 is mounted in a cavity 110 on the housing 104. As shown in FIG. 1, there is a post 112 for mounting acoustical sensing apparatus 100 to the friction weld device 114. Post 112 is connected to housing 104 at a proximal end.

As shown in FIG. 1, acoustical sensing apparatus 100 is mounted in such a way so that acoustical sensor 102 does not contact work piece material 106, segmented collet 108 or segmented flywheel 116. Additional, the acoustical sensor 102 does not contact the friction weld device 114. This allows to the acoustical sensing apparatus to operate as a noncontact acoustical sensing apparatus.

Figure 2A:
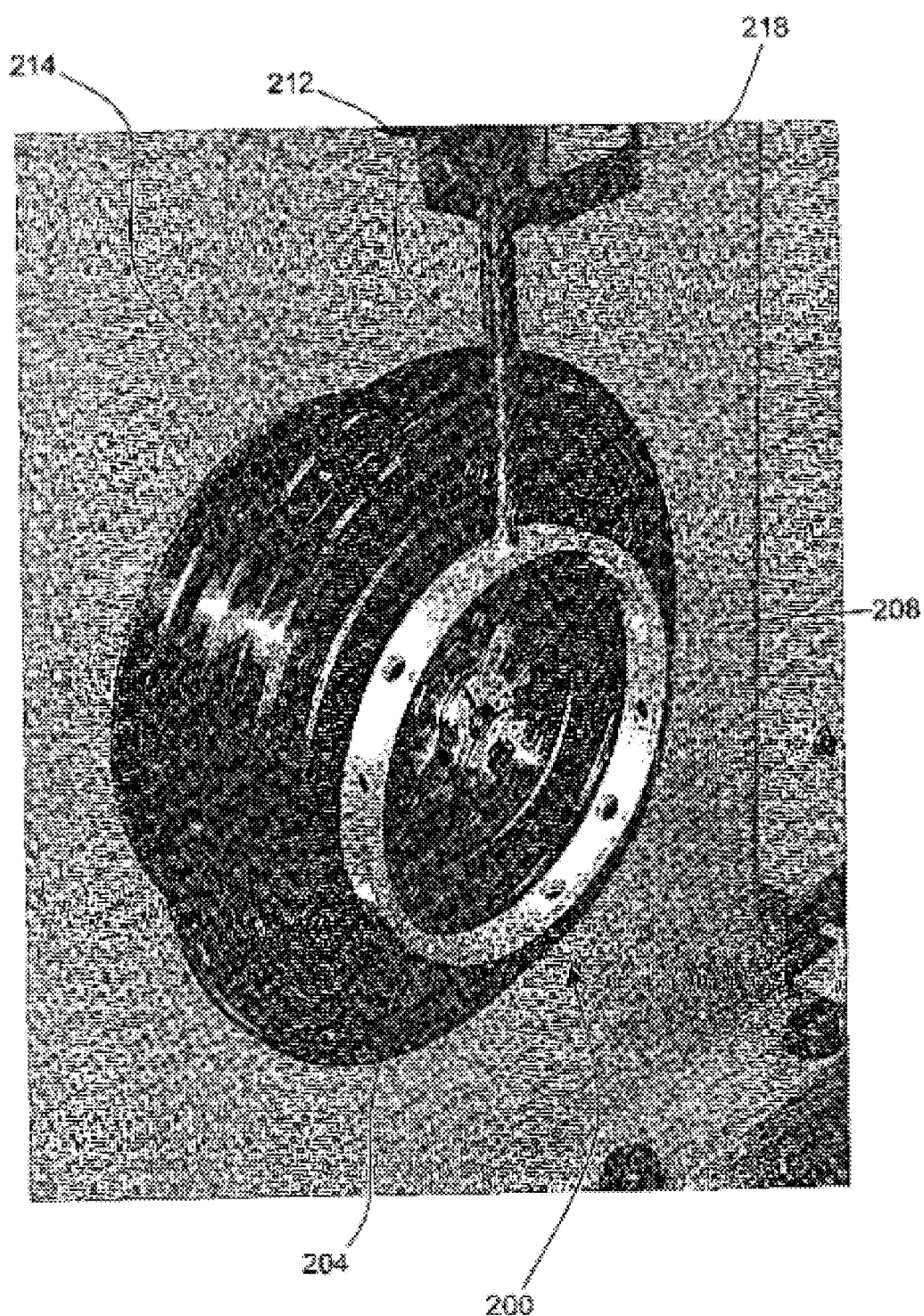
FIG. 2A is a photograph having a left perspective view of a housing mounted on a friction weld device constructed in accordance with a preferred embodiment of the invention.
Figure 2B:
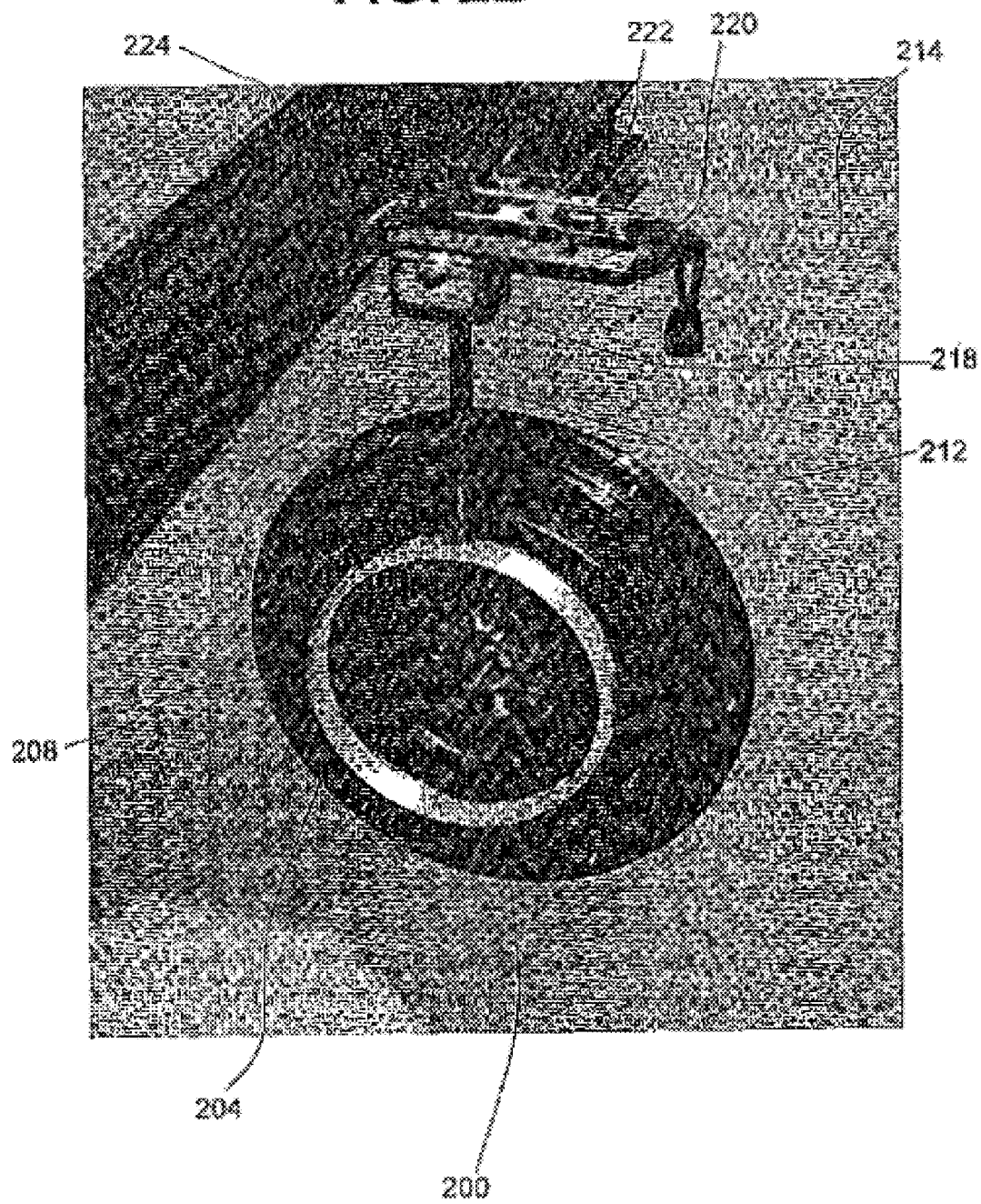
FIG. 2B is a photograph having a right perspective view of a housing mounted on a friction weld device constructed in accordance with a preferred embodiment of the invention.
Figure 2C:
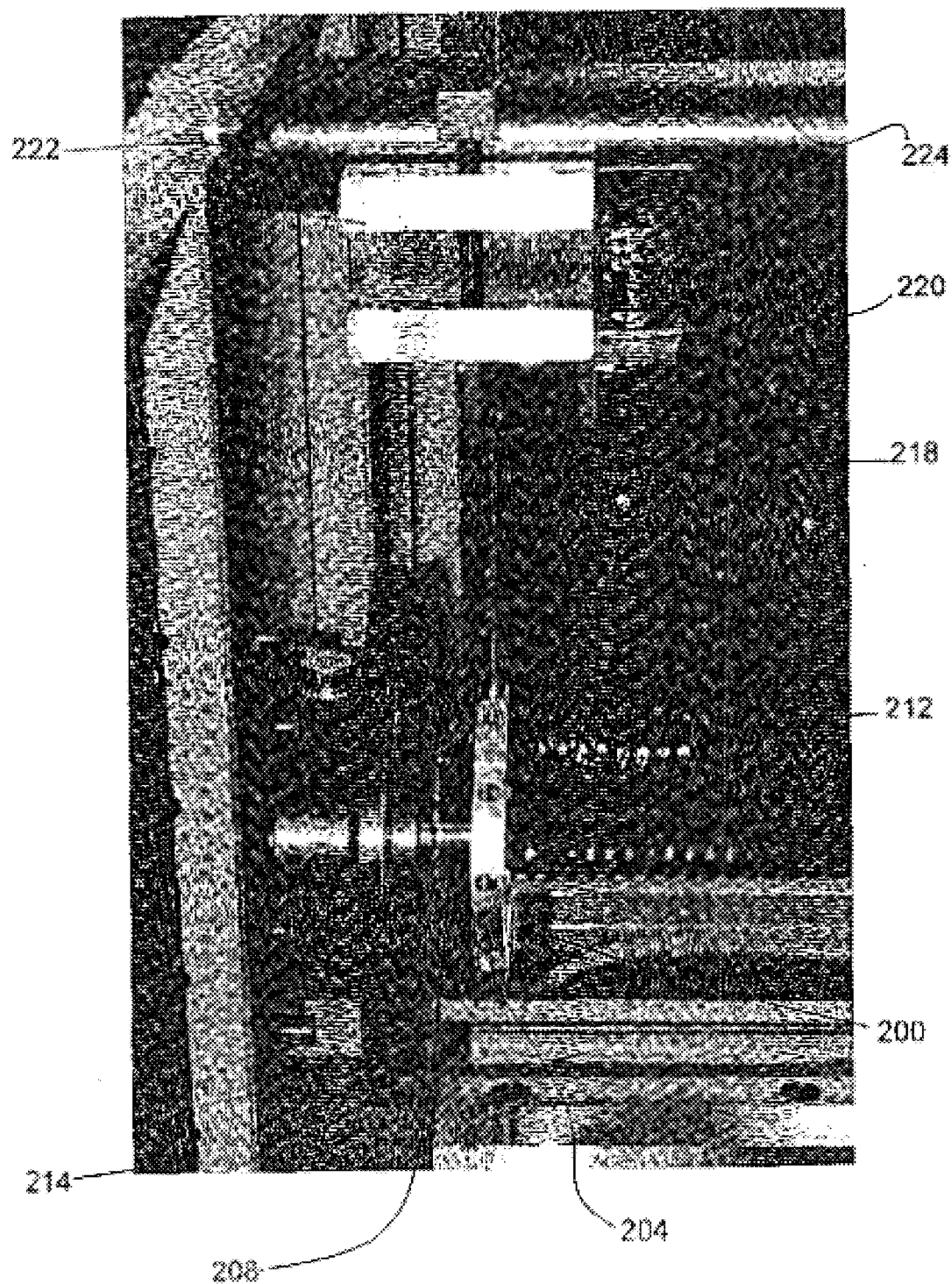
FIG. 2C is a photograph having a side view of a housing mounted on a friction weld device constructed in accordance with a preferred embodiment of the invention.

FIGS. 2A, 2B and 2C show a preferred embodiment of the present invention including an acoustical sensing apparatus 200 having a housing 204 that surrounds a segmented collet 208. A post 212 mounts acoustical sensing apparatus 200. Post 212 is connected to housing 204 at a proximal end. A base indicator 218 is connected to post 212 at a distal end. Base indicator 218 is connected to level 220 which are both connected to a clamp 222. Clamp 222 is connected to a bar 224 which extends out from the friction weld device 214.

Preferably, the acoustical sensing apparatus is an acoustic ring assembly. Preferably, the housing is shaped as aluminum ring. Preferably, the acoustical sensor is a microphone. Other acoustical sensor may be used such as a piezoelectric transducer, etc. Preferably, the means for mounting is attached to the friction weld device by a clamp connected to a bar. The bar may be substantially parallel to the work piece material in the segmented collet. The means for mounting the housing may also be attached to the floor or ceiling. The post may be used as a means for mounting and the post is preferably ⅛ to ⅝ inch in diameter and most preferably is ⅜ inch in diameter.

Preferably, the housing should have one to twelve cavities. Multiple cavities should be an equal distance from every other cavity on the housing. The diameter of the cavities for mounting the sensors is preferably ¹⁄₁₆ to 2 inch. More preferably, the diameter is ⅛ to ⅝ inch. Most preferably the diameter is ³⁄₁₆ inch.

Preferably, the base indicator and level and connected by means of a magnet. The level keeps the acoustical sensor in level position with regards to the friction weld device. The level may also keep the acoustical sensor in a position so that the acoustical sensors at an equal distance from the work piece material in the segmented collet.

Figure 3A:
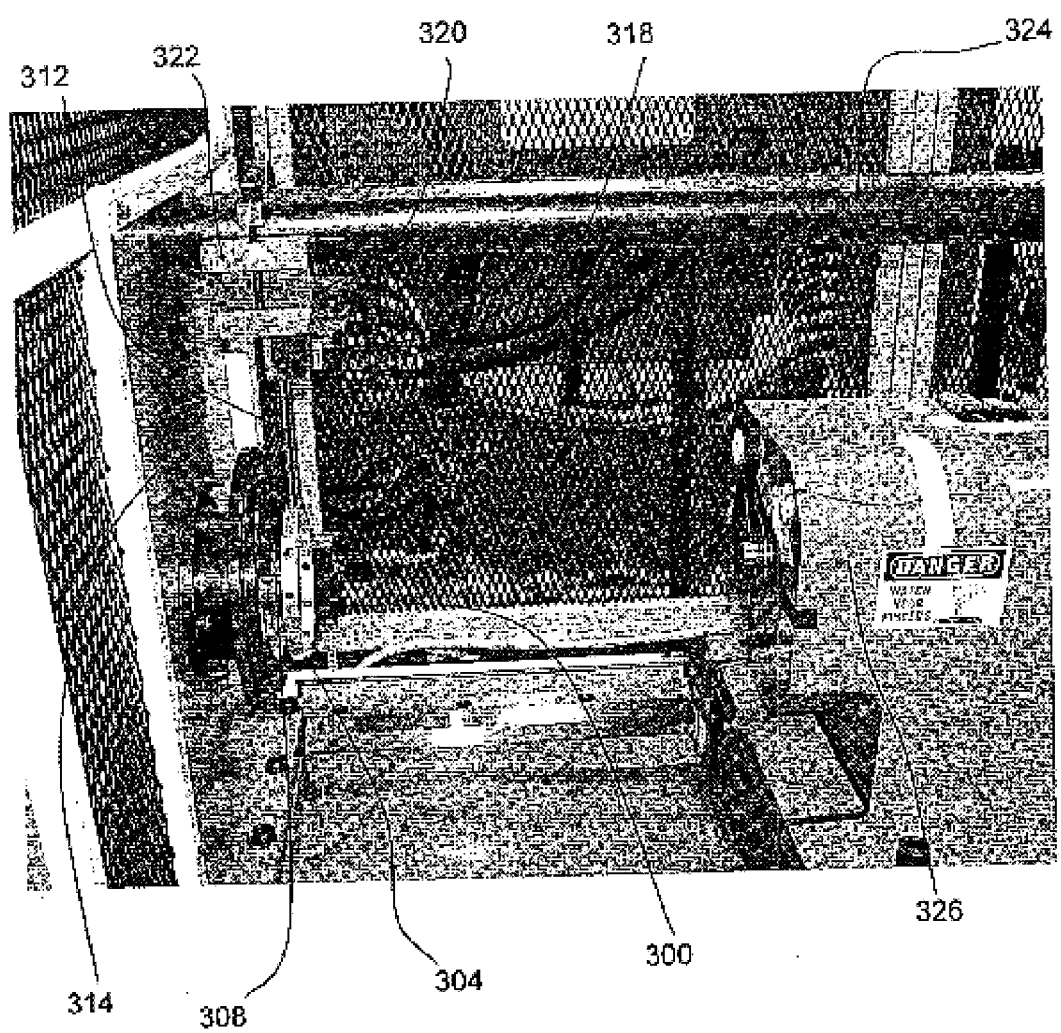
FIG. 3A is a photograph having a side view of a housing mounted on a friction weld device with the ram pulled back constructed in accordance with a preferred embodiment of the invention.
Figure 3B:
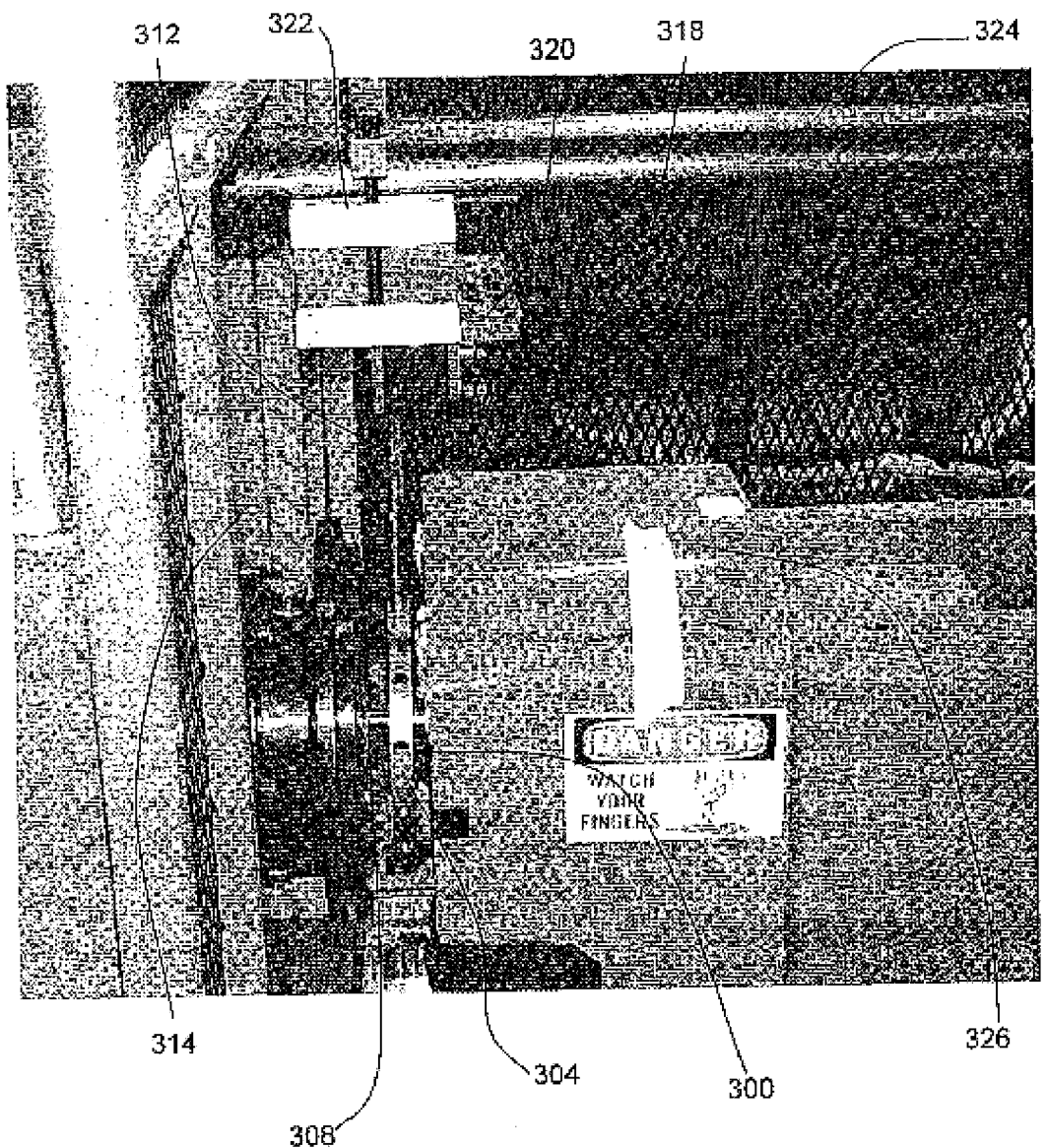
FIG. 3B is a photograph having a side view of a housing mounted on a friction weld device with the ram pushed forward constructed in accordance with a preferred embodiment of the invention.

FIGS. 3A and 3B show a preferred embodiment of the present invention including an acoustical sensing apparatus 300 having a housing 304. A post 312 mounts acoustical sensing apparatus 300. Post 312 is connected to housing 304 at a proximal end. A base indicator 318 is connected to post 312 at a distal end. Base indicator 318 is connected to level 320 which are both connected to a clamp 322. Clamp 322 is connected to a bar 324 which extends out from the friction weld device 314.

As shown in FIG. 3A, a ram 326 may hold the second work piece material. Friction weld device 314 may hold a first work piece material. As shown in FIG. 3B, ram 326 is moved toward friction weld device 314 so that a friction weld may be formed using both work piece materials. As shown in FIG. 3B, acoustical sensing apparatus 300 does not contact either the ram 326 or the friction weld device 314.

Figure 3C:
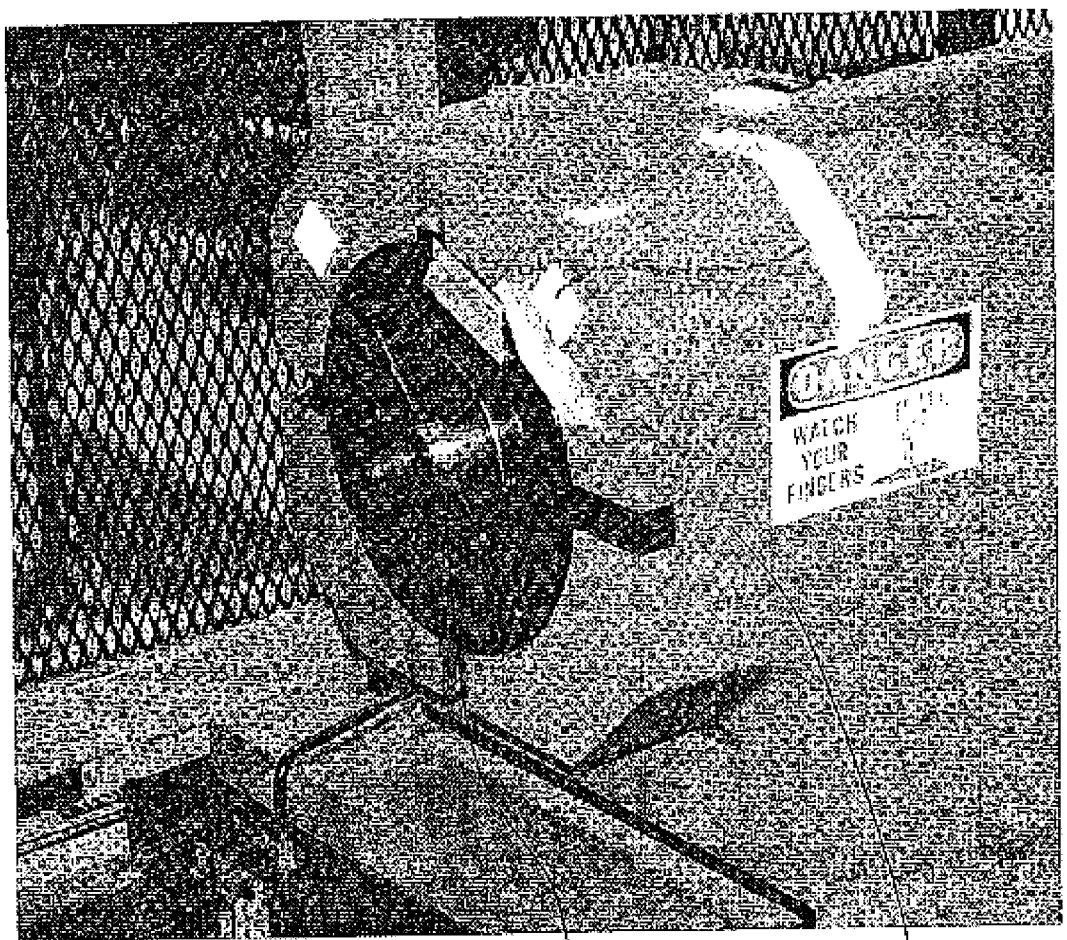
FIG. 3C is a photograph having a perceptive view of the ram of a friction weld device constructed in accordance with a preferred embodiment of the invention.

FIG. 3C shows a ram 326 having a second segmented collet 328. Second segmented collet 328 may hold a second work piece material (not shown) that can be used to form a friction weld.

Acoustical sensing apparatus of the present invention samples the acoustical emission/energy (AE) or acoustical signature in the form of sound pressure that is emitted during the friction welding processes, such as the plastic deformation and phase transformation. The acoustical sensing apparatus may be able to sample at least the rapid release of energy, such as sound or pressure, due to mechanical, thermal and metallurgical phenomenon that may occur during welding.

The noncontact acoustical sensing apparatus of the present invention may be used to identify features within the acoustical emission or acoustical signature of an inertia-friction weld that are indicative of weld characteristics, such as bond quality. A probabilistic neural network (PNN) may be used to analyze the acoustical emission's frequency information to classify acceptable, conditional, and unacceptable welds. A pattern classification process may be used to further classify weld qualities of weld joints.

Pattern classification is only one of several forms of pattern recognition. Other commonly applied pattern recognition techniques include estimation, prediction, and control. The methodology of pattern classification for the present invention may be similar to the methodology described in Bezdek, J., *Journal of Intelligent and Fuzzy Systems*, 1, 1–25 (1993), the entire contents of which are hereby incorporated by reference.

Figure 4:
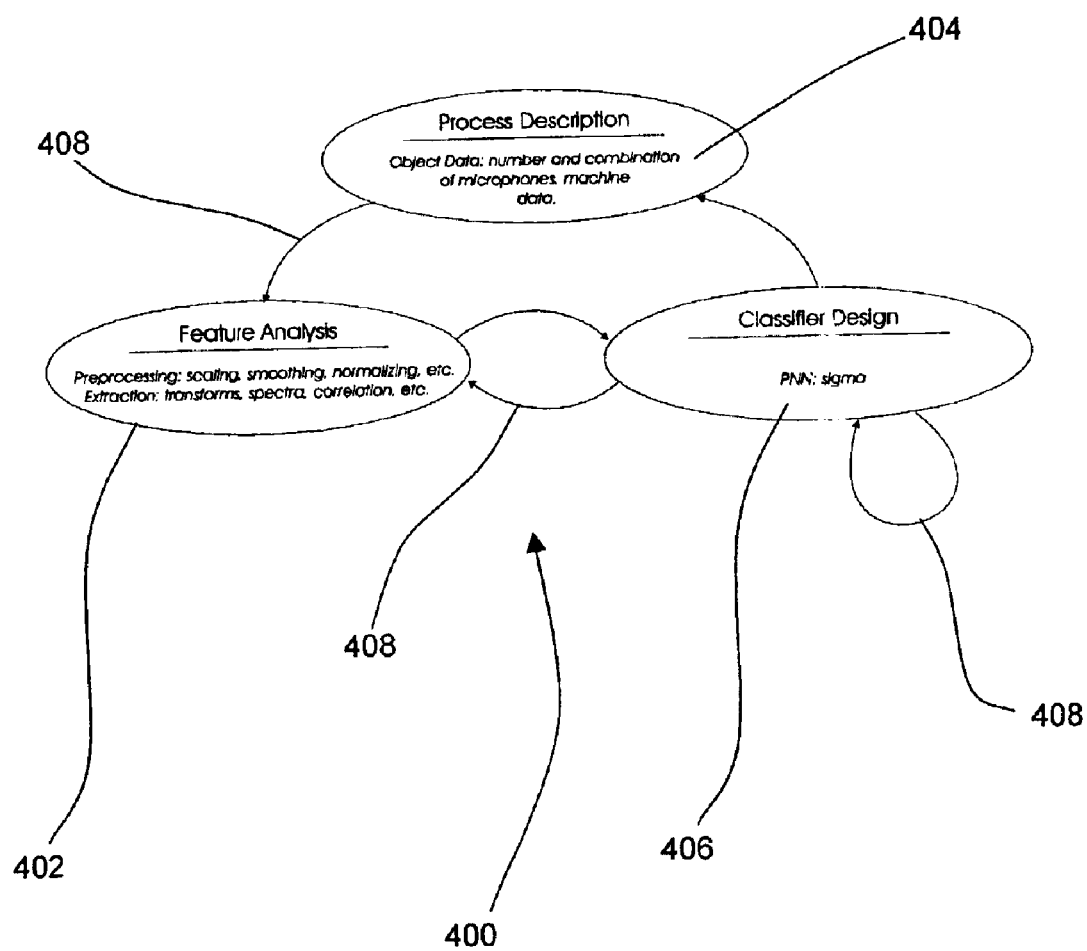
FIG. 4 is a diagram of a pattern classification system constructed in accordance with a preferred embodiment of the invention.

FIG. 4 shows the pattern classification system 400 of the present invention. Pattern classification system 400 involves iteratively revisiting the three modules, feature analysis 402, process description 404, and classifier design 406. Modifications, shown by arrows 408, to a module results in re-evaluating the pattern classification system 400 performance. The revisiting of the module continues until pattern classification system 400 (1) satisfied a given set of performance requirements and economic constraints or (2) failed to yield any acceptable results.

The process description module of the present invention may be captured with machine process data, such as speed, pressure and upset, and acoustical energy. Previous research as described in Hartman, D., Cola, M., and Dave, V., "Eliminating Post-Process Inspection of Inertia Friction Welds Through In-Process, Quality-Based Monitoring," in *82nd Annual AWS Convention, Abstracts of Papers*, Cleveland, Ohio, 2001, pp. 190–192, the entire contents of which are hereby incorporated by reference, demonstrated the ability to detect and classify various defective conditions in similar material, tubular inertia-friction welds using only machine process data.

The process description module of the present invention may determine the possible combination of sensing data that may yield classifiable features. Once the process description module is determined, the next step is feature analysis module. Feature analysis represents techniques that explore and improve upon raw data. Two methods of feature analysis are preprocessing, such as scaling, smoothing, interpolating and normalizing, and extracting, such as discrete Fourier transform and spectrogram.

Classifier design module functions to find a partition within the process description data that yields a computationally explicit, e.g., discriminant functions and/or nearest prototype rules, or implicit, e.g., multilayered Perceptrons and/or k-nearest neighbor rules, decision function. A supervised classifier design using a probabilistic neural network (PNN) may be used. The smoothing parameter, a, is the only parameter affecting the performance of a basic PNN.

Figure 5:
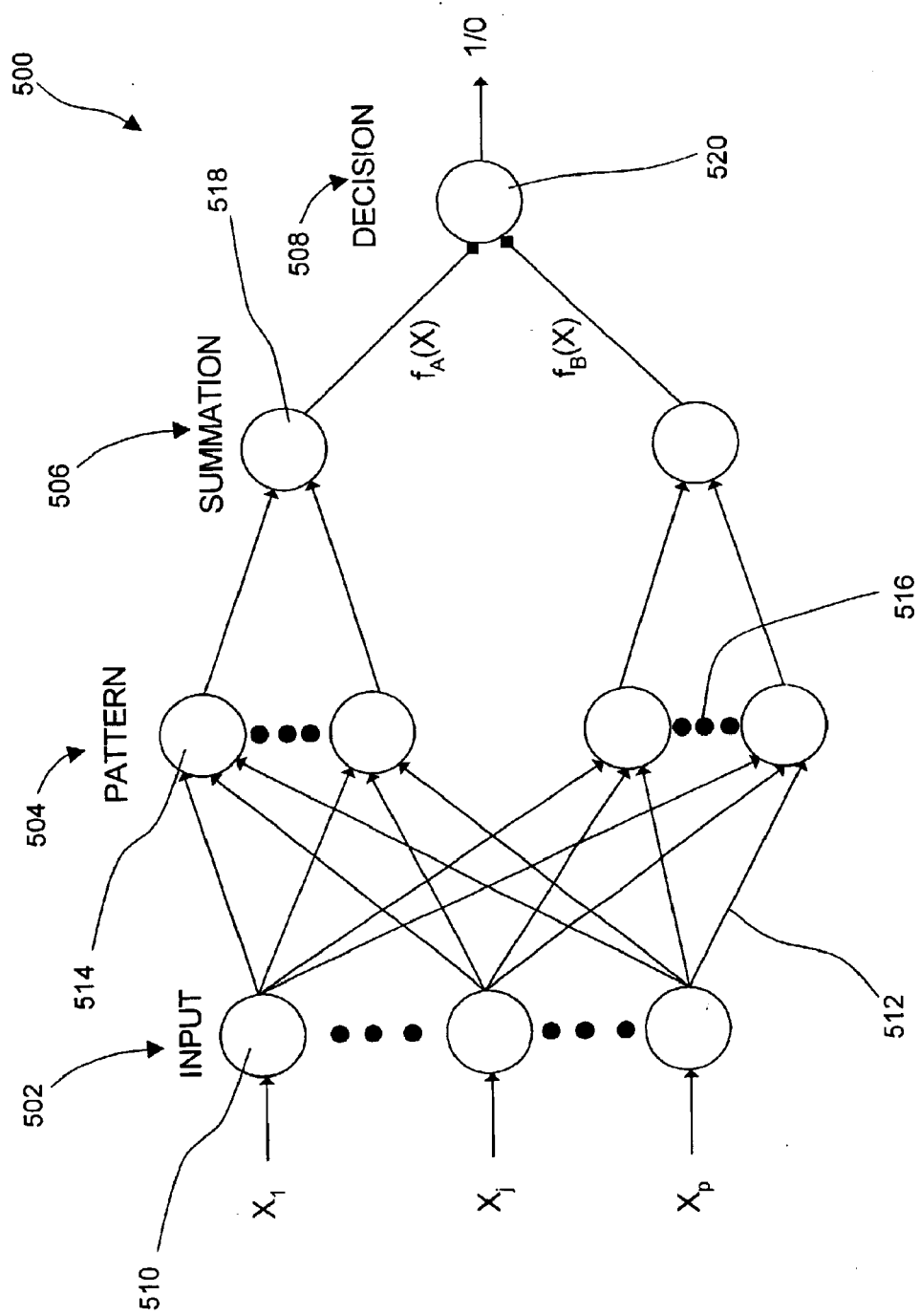
FIG. 5 is a probabilistic neural network (PNN) architecture for a two-category decision network constructed in accordance with a preferred embodiment of the invention.

The development of PNN is described in Specht, D., "Probabilistic Neural Networks for Classification, Mapping or Associative Memory," in *Proceedings of the IEEE International Conference on Neural Networks*, 1988, vol. 1, pp. 525–532, and Specht, D., *Neural Networks*, 3, 109–118 (1990), the entire contents and disclosure of which are hereby incorporated by reference. The PNN is a feed forward neural implementation of Bayesian classifiers that provides a framework for solving pattern classifications. FIG. 5 illustrates a two-category decision architecture for the Basic PNN. Other, more complex, implementations of a PNN exist including adaptive learning techniques and clustering algorithms. Any type of PNN may be used for the present invention.

FIG. 5 is a two-category decision network 500 consisting of four neural layers: input 502, pattern 504, summation 506, and decision 508. Each layer has a different and specific function. The two-category decision network 500 may be organized based on an input matrix that is represented by a p-dimensional vector, $X^1=[X_1 \ldots, X_j \ldots, X_p \ldots J]$. The input units 510 distribute the same input values 512 to all of the pattern units 514 in the network 500, i.e. the two layers are full connected. The input units may consist of acoustical data and/or observed data. Each pattern unit 514 calculates the dot product 516 of the pattern vector X with the weight vector $W_i$:

$$Z_i = X \cdot W_i \qquad \text{Equation 1}$$

and then applies a nonlinear activation function, such as an exponential function to give each pattern neuron its output:

$$g(Z_i) = \exp[(Z_i\ 1)/\sigma^2] \qquad \text{Equation 2}$$

where σ is the smoothing parameter. When X and W are normalized to unit length, Equation 2 represents a simplification of Parzen's probability density function (PDF) estimator, as described in Parzen, E., *Annals of Mathematical Statistics*, 33, 1065–1076 (1962), the entire contents of which are hereby incorporated by reference.

Since a priori knowledge in a typical neural network classification problem is the training patterns, the training patterns in the implementation of a Basic PNN therefore provide the probability densities for the categories to be separated. As such, the Basic PNN uses one pattern neuron for each pattern in the training set.

As shown in FIG. 5, the summation layer 506 contains one summation unit 518 per category. Each summation unit 518 sums the outputs from the pattern units 514 that are associated with its category. The output of the summation neurons is then passed to the decision layer neurons 520. The decision neurons 520 implement Bayes' strategy for classification as described in Gelman, A., Carlin, J., Stern, H., and Rubin, D., *Bayesian Data Analysis*, CRC Press, Boca Raton, Fla., 1995, 1st edn., the entire contents of which are hereby incorporated by reference.

Bayes' strategy for classification minimizes the expected risk by implementing Bayes decision rule. For a two-category problem, Bayes decision rule becomes:

$$d(X) = \begin{cases} \Theta_A & \text{if } h_A l_A f_A(X) > h_B l_B f_B(X) \\ \Theta_B & \text{if } h_A l_A f_A(X) < h_B l_B f_B(X) \end{cases} \qquad \text{Equation 3}$$

where: $h_A$ is the a priori probability that the input pattern is form category A; $h_B$ is the a priori probability that the input pattern is form category B($h_B=1-h_A$ for two-category problems); $I_A$ is the loss associated with the incorrect decision, i.e., $d(X)=\theta_B$ when $\theta=\theta_A$; $I_B$ is the loss associated with the incorrect decision, i.e., $d(X)=\theta_A$ when $\theta=\theta_B$.

The decision layer neurons 520 are two-input neurons that produce a binary output based on a single variable weight:

$$C = \frac{h_B l_B}{h_A l_A} \cdot \frac{n_A}{n_B} \qquad \text{Equation 4}$$

where $n_A$ equals the number of training patterns from category A and $n_B$ equals the number of training patterns from category B. In general, the values for calculating the ratio C are determined by the use relative to the significance of the decision. When there is no reason to bias the decision, then the ration C may be simplified to an inverter, i.e., C=−1.

Training may be accomplished by iterating only once through the training vectors. For each training pattern: (1) a new pattern neuron is created, (2) its weight vector $W_i$ is set equal to each of the X values in the training pattern, and (3) the output of the pattern neuron is connected to the appropriate summation unit. Several important consequences may arise out of the PNN's unique architecture and training method. First, a PNN can begin classifying after having just one training pattern from each category. Second, a PNN is orders of magnitude faster to train than a traditional back propagation neural network. Third, a PNN can be shown to asymptotically approach Bayes' optimal decision surface without the possibility of getting stuck in local minima. Fourth, a PNN architecture is conductive to enabling a human to understand how the network works. A PNN is a preferred means used by the method of the present invention for exploring data sets in which the structure is ill-defined and that contain both deterministic and random signals. The present invention may also use other pattern classification techniques, such as, adaptive probabilistic neural network, fuzzy classification, linear discriminant analysis, other multi-layer neural networks, and unsupervised learning and clustering techniques.

The present invention may be used with a variety of solid-state welding techniques. Solid-state welding techniques are different from arc welding in that solid-state welding techniques do not require shielding gases, fluxes, and filler metal to achieve a bond between two materials. Solid-state welding is the preferred method of joining materials in which melting, and hence mixing, of the base materials is not desired. Solid-state welding (SSW) processes accomplish joining by applying pressure or pressure and heat to the workpiece to form a metallurgical bond. The temperature at which joining is performed is well below the melting point but at or above the forging temperature of the base metal.

There are several types of solid-state welding techniques that are described in the Welding and Joining Handbook, American Welding Society, Vol 1. ($9^{th}$ Ed. 2001), the entire contents of which are hereby incorporated by reference. Two of the preferred solid-state welding techniques of the present invention are friction welding, including direct drive friction welding and inertia drive friction welding, and friction stir welding. Friction welding (FRW) converts mechanical energy into heat through rotational and compressive forces that are applied to the work-piece materials. The two major process variations of friction welding exist: (1) direct drive friction welding (sometimes called conventional friction welding) and (2) inertia drive friction welding (commonly referred to as inertia friction welding or flywheel friction welding). Inertia friction welding relies on the kinetic energy stored in the rotating flywheel to be dissipated as heat due to the frictional forces at the faying surfaces. In contrast, direct drive friction welding utilizes a motor-driven rotational force that translates force into heat. The rotation is maintained for a fixed period of time and is stopped by the application of a braking force.

In both processes, a friction-welding machine rotates one part while the other is held stationary and forces them together. FIGS. 11A–11E display a schematic illustration of the stages of the friction welding process of a preferred embodiment of the present invention. In FIG. 11A, stage one involves compressed work-piece 1102 and a rotating work-piece 1104. Compressed work-piece 1102 does not rotate or move. Rotating work-piece 1104 is rotate at a predetermined speed. In FIG. 11B, stage two involves compress ing compressed work-piece 1102 into rotating work-piece 1104. An axial force is applied between compressed work-piece 1102 and rotating work-piece 1104. In FIG. 11C, the compressive and frictional forces produces heat causing the displacement of the material or flash 1106 at the faying surface 1108 of the compressed work-piece material 1102 and the faying surface by 1110 of the rotating work-piece The frictional heat raises the material to its forging temperature while pressure is applied to create the weld. In FIG. 11D, rotation of rotating work-piece 1104 is stopped and axial force is maintained for a predetermined amount of time to complete the weld joint 1112.

Friction stir welding is a variation of the friction welding process. The friction stir welding was developed at The Welding Institute (TWI). The friction stir welding process applies a nonconsumable rotating tool between the faying surfaces of a butt joint while the workpieces are firmly held in place. The tool is pushed down, i.e., plunged, into the material to a preset depth. Once plunged, a weld is produced through the generation of a high enough temperature that allows stirring of the hot metal as the tool travels along the length of the joint. Unlike the friction welding processes, both direct and inertia, the work-piece in the friction stir welding process is restricted from movement while a rotating tool generates frictional heat and, thereby, induces gross plastic deformation of the work-piece material.

As shown in FIG. 12, there is a friction stir welding machine 1200. A tool 1202 of friction stir welding machine 1200 is composed of a steel shaft 1204 and a pin 1206. Tool 1202 is mounted in a spindle 1208. In the first stage of the friction stir welding process, a butt joint 1210 is formed by mating the edges of two work-pieces 1212 and 1214. A means for fixing (not shown) two work-pieces 1212 and 1214 is preferred to prevent spreading or lifting of the work-pieces during the friction stir weld process. In the second stage, tool 1202 is rotated at a predetermined spindle speed. In stage 3, tool 1202 plunges into the work-pieces 1212 and 1214 at the butt joint 1210 to a preset depth. Pin 1206 of tool 1202 travels into the work-pieces 1212 and 1214. Friction stir welding machine 1200 traverses along the butt joint 1210 to form the weld joint 1216.

The acoustical sensing method and device of the present invention may be placed in a position to surround the tool or swindle of the friction stir weld machine to collect acoustical data from the function weld. Preferably, the position would not contact the work-pieces.

EXAMPLE 1

In one example of the preferred embodiment of the present invention, bar-to-bar inertia friction welding of copper to 304 L stainless steel was used. This material combination exhibits only marginal weldability and is ideally suited for validating the capabilities of the preferred embodiment of the present invention.

In this example, oxygen-free, high-conductivity (OFHC) copper bar nominally 1-inch diameter and annealed Type 304L stainless steel bar nominally 0.5-inch diameter were used. OFHC copper is essentially 99.99 percent pure, while 304 L is a low carbon grade of austenitic stainless steel. About three weeks before welding each specimen was given a preliminary machining step to ensure a faying surface finish of 32 $\mu$in.

In this example, welding was conducted using an MTI Model 90B inertia friction welding system. Initial parameter selection was based upon work described in Bell, R. A., Lippold, J. C., and Adolphson, D. R., *Welding Journal*, 63, 325s–332s (1984), the entire contents and disclosure of which are hereby incorporated by reference, but altered slightly by this example to accommodate differences in available inertial mass. The welding parameters remained constant throughout this investigation and are shown in FIG. 6.

Selected copper specimens were machined immediately before welding while bathed in isopropyl alcohol. Others were welded as-is, i.e., without further machining to remove surface oxidation that might have occurred while at ambient temperature and pressure for up to five weeks prior to welding. In all cases, the stainless steel was rotated during the weld cycle while the copper remained fixed. Lastly, the specimens extended from the spindle and fixture collets by approximately one diameter.

A noncontact acoustical sensing apparatus, having an array of acoustical sensors, surrounds the weld joint and may be used to collect the rapid release of energy (sound pressure) due to the mechanical, thermal, and metallurgical phenomenon occurring during friction welding. The acoustical sensors used in this example are off-the-shelf electret condenser microphones.

The noncontact acoustical sensing apparatus accurately measures sound pressures at audio frequencies in the air. Up to twelve microphones can be held in the housing. FIG. 1 illustrates a preferred embodiment used in this example, in which four microphones are evenly placed in the housing. FIGS. 2A–3C illustrate a preferred embodiment of the acoustical sensor mounted to the friction weld device used in this example.

The acoustical signature was sampled at 40 kHz per channel. Calibration of the microphones was accomplished by comparing it to a calibrated Brüel & Kjaer condenser microphone, type 4133, within the frequency sensitivity range of the sensor's microphones.

Standard metallographic procedures were used to prepare selected specimens to a 1-$\mu$m finish. Microstructural features were revealed by using a double etching procedure comprising a 5% ammonium persulphate etch for the OFHC copper followed by an electrolytic 10% oxalic acid etch for the stainless steel. Light microscopy up to 100× magnification revealed salient features of the bond interface and surrounding heat and deformation zone (HDZ).

A semi-quantitative evaluation of each weld joint was performed using unguided bend testing. As-welded, full-size specimens were tested. Image analysis techniques were used to determine the percent of bonded area after fracturing each specimen. A microharness survey was conducted across the joint interface using a 200 g load and Vickers indenter for a dwell time of 15 seconds.

A probabilistic neural network (PNN) was used as the classifier in this example.

A series of neural network trainings and trials was performed in an effort to search for features that could be used to correlate the acoustical signature or AE data to weld bond quality. As shown in FIG. 4, any modifications to either the process description, feature analysis, or classifier design resulted in re-running the system and evaluating its performance. The variables listed in FIG. 7 were modified during the iterative development of the pattern recognition system.

Three different classifications were investigated: (1) acceptable and unacceptable, (2) acceptable and conditional, and (3) acceptable, conditional, and unacceptable. A moving window discrete Fourier transform (DFT) was performed on the acoustical signature or AE data using the fast Fourier transform (FFT) algorithm. A step size of 250 data points was used to move through the time-domain data (120,000 samples, 3 seconds at 40 kHz) without overlap.

Each segment of the time-domain data was filtered using a Hanning Window and then transformed into the frequency domain. Finally, the transformed data was then normalized prior to including it in the training patterns as acoustical data for the PNN. For multiple microphones, the normalized and transformed data was appended to the other microphone's transforms before including it in the training patterns as acoustical data for the PNN.

Each window increment within the acoustical data resulted in a complete training and testing of the PNN's ability to classify bond quality. Training consisted of (1) removing one pattern from the training data, (2) training the PNN, and (3) testing the PNN with the removed pattern. This was repeated for each pattern within the set. The PNN's accuracy in classifying bond quality was then determined by summing the total number of correct classifications and dividing by the total number of training patterns.

The result of this training and testing phase will yield a graph showing classification accuracy vs. time. This graph identifies the location of features within the acoustical signature that can be used to infer bond quality. Once this is determined, future work can improve upon the process description, feature analysis, and classifier design in an effort to build a robust, in-process monitoring system for inertia friction welding and, potentially, for other friction welding processes.

The training/testing method used in this example was motivated out of a limited size of the available data set. Commonly referred to as the single holdout method, the training/testing method holds out one data point from the n-sized data set for testing while the remaining n−1 data points in the data set are used for training. This procedure is repeated until all data points in the data set have been tested independently. Classification accuracy is calculated based on the sum of the correctly classified data points minus the sum of the incorrectly classified data points divided by n.

Although the experimental matrix was designed with only one variable in mind (surface preparation of the copper), three different quality welds were generated: (1) Acceptable: bonded area is approximately 100%; (2) Conditional: bonded area is less than 100% but greater than 5%; and (3) Unacceptable: bonded area is less than 5%.

FIG. 8 is a table showing the conditional weld joints were prepared in the same manner as the acceptable weld joints, namely by freshly machining the work piece materials. This demonstrates the difficult nature of joining these two work piece materials.

After welding, each specimen was visually inspected for uniformity and color of weld flash. FIGS. 9A–9F illustrates a typical flash and fracture surface for each category of weld. All specimens exhibited a symmetric flash with a light golden color. Moreover, the amount of upset (or reduction in length [RIL]) was approximately equal and predominately occurred in the copper. Moreover, the fact that the RIL's were approximately equal, yet acceptable, conditional, and unacceptable welds resulted, suggests that RIL alone is an insufficient measure of bond quality as shown in FIG. 8.

Specimens that were machined immediately before welding exhibited a copper-side HDZ that was uniform across the diameter—as expected. This type of HDZ shape indicates that the part's speed was at least sufficient to ensure center heating. Specimens that were welded as-is had a HDZ shape that was narrowest at the center indicating insufficient heat generation not from lack of speed since all parameters remained constant, but rather due to insufficient oxide removal during the upset/forging phase. The microstructural features observed on each side of the joint interface were as expected given the large difference in yield strength between the copper and stainless steel. At high magnification, the interface of a typical as-welded specimen exhibited no apparent discontinuities or lack of bonding. However, the refined grain size on the copper side of the interface is readily distinguishable from the stainless steel where a very narrow band (approximately 5 $\mu$m) of deformation appears immediately adjacent to the interface.

Qualitative bond area from unguided bend test results are summarized in FIG. 8 and illustrated in FIGS. 9A–9F. In this example, the test results are semi-quantitative because the actual force required for failure was not measured. Nonetheless, sufficient information exists to render a determination of acceptable bond quality based on fracture surface morphology and percent of interface area bonded. Image analysis of the fracture surfaces provided a reasonable approximation of the percent of interface area bonded for specimens exhibiting less than 100% bonding.

In FIG. 9A, there is a copper rod 902 that is welded to a stainless steel rod 904. A flash 906 is shown between copper rod 902 and stainless steel rod 904. In FIG. 9B, there is a copper rod 902' that is welded to a stainless steel rod 904'. A flash 906' is shown between copper rod 902' and stainless steel rod 904' In FIG. 9C, there is a copper rod 902" that is welded to a stainless steel rod 904". A flash 906" is shown between copper rod 902" and stainless steel rod 904".

In FIG. 9D, a copper rod 910 has a bonded area 912 and a stainless steel rod 914 has a bonded area 916. In FIG. 9E, copper rod 910' has a bonded area 912' and stainless steel rod 914' has a bonded area 916'. In addition, copper rod 910' has an unbonded area 918' and stainless steel rod 914' has an unbonded area 920'. In FIG. 9E, copper rod 910" has an unbonded area 918" and stainless steel rod 914" has an unbonded area 920".

Specimens having acceptable bond quality exhibited ductile tearing through the copper without any lack of bonding, as shown in FIGS. 9A and 9D. Specimens having a conditional bond quality are shown in FIGS. 9B and 9E. Specimens having an unacceptable bond quality are shown in FIGS. 9C and 9F. However, all of the specimens that were welded as-is, i.e., not freshly machined, exhibited a lack of bonding over the majority of the interface. Generally, the as-welded specimens exhibited little to no ductile features on the fracture surfaces. Lastly, there are those specimens that exhibited conditional bond quality and are order ranked between acceptable and unacceptable as shown in FIG. 8.

Figure 10A:
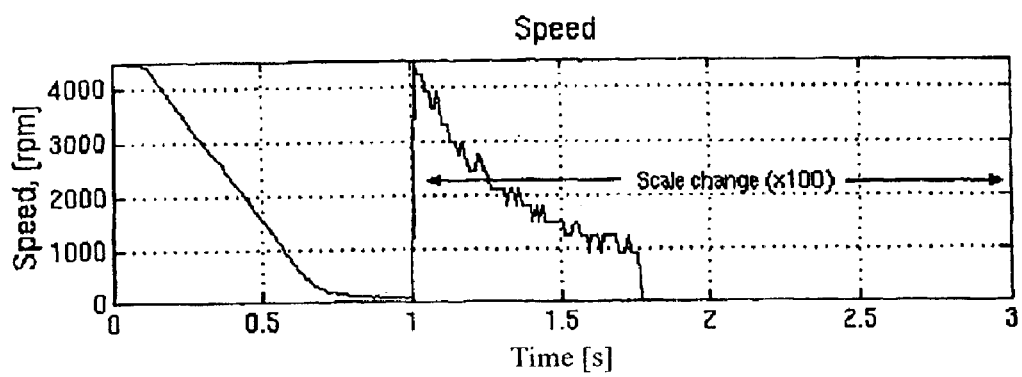
FIG. 10A is a speed versus time chart for the friction weld process showing the rotational speed of one work piece in example one of the invention.
Figure 10B:
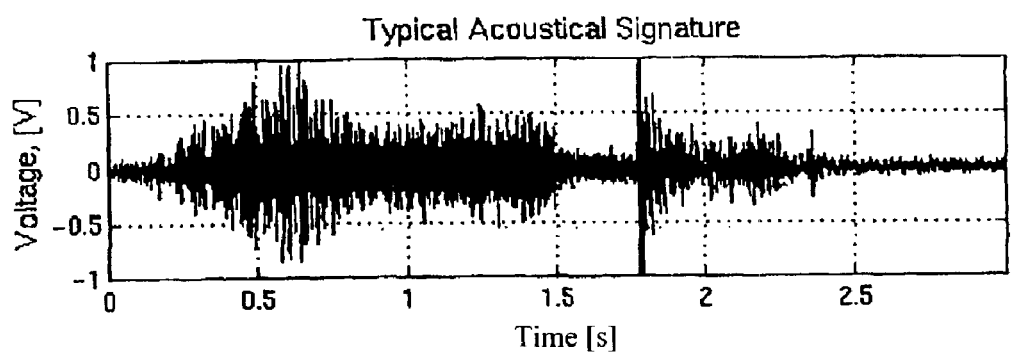
FIG. 10B is a voltage versus time chart for the acoustical signature sampled by an acoustical sensor in example one of the invention.

FIGS. 10A–10E illustrates the results from this example. In this example, four microphones yielded improved accuracy over one microphone and was comparable to or better than two microphones. FIG. 10A, graphically represents the rotating speed involved in the friction weld process of this example. FIG. 10B, graphically represents the typical acoustical signature from a weld joint.

Figure 10C:
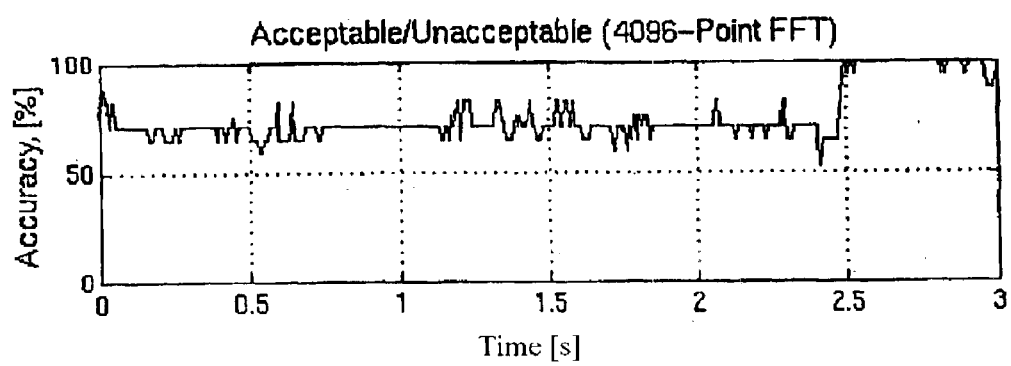
FIG. 10C is an accuracy versus time chart for the classification system using acceptable/unacceptable quality categories produced by a trained neural network in example one of the invention.

As shown in FIG. 10C, acceptable and unacceptable bond quality can be reliably detected under most parameter combinations that were investigated. This example showed that the differences in the copper's surface preparation manifested in the acoustical signature at the end of the weld. Specifically, in the time period at approximately 2.5 seconds to 3 seconds, an acceptable bond quality was determined.

Figure 10D:
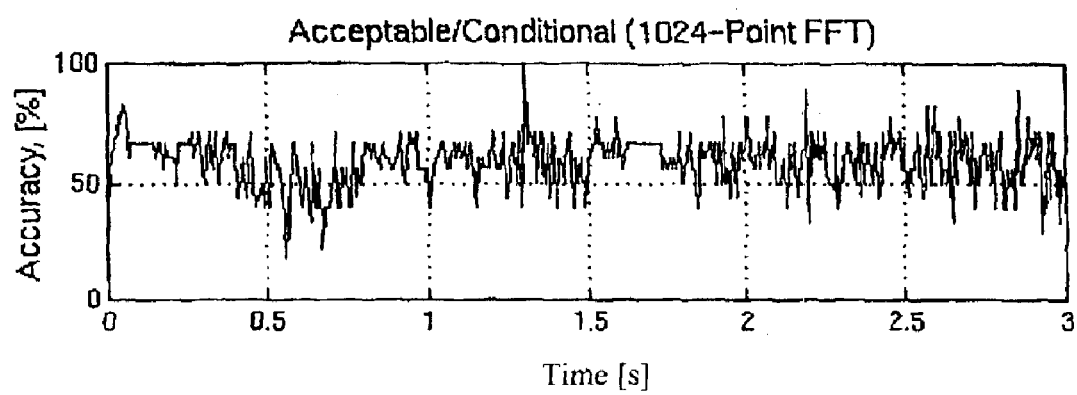
FIG. 10D is an accuracy versus time chart for the classification system using acceptable/conditional quality categories produced by a trained neural network in example one of the invention.

As shown in FIG. 10D, acceptable and conditional bond quality was detected in but further work needs to be performed to verify and enhance this result. The features for distinguishing between an acceptable and conditional bond appear at a different location within the acoustical signature than they do for an acceptable and unacceptable bond. In particular, conditional bond quality is detected at approximately 1.3 seconds after contact is made between the faying surfaces.

Figure 10E:
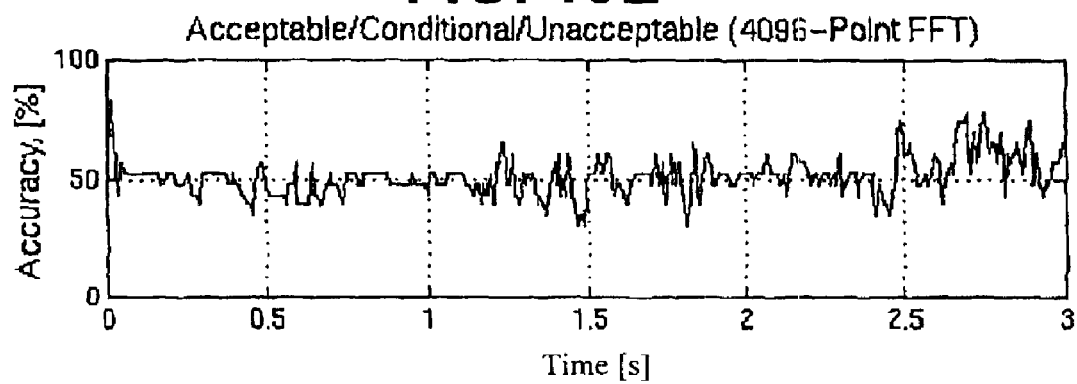
FIG. 10E is an accuracy versus time chart for the classification system using acceptable/conditional/unacceptable quality categories produced by a trained neural network in example one of the invention.

For this result, the classification system was unsuccessful at finding three partitions within the data space that could accurately identify and discriminate between the three different bond quality classes, as shown in FIG. 10E. It is possible that the classifier's inability to discriminate between all three classes is due to an insufficient number of training vectors. Furthermore, additional feature analysis techniques and improved learning algorithms might rectify this shortcoming.

The results produced by this example showed a successful bond quality classification system which used a novel, non-contact, acoustical emission sensing technique that: (1) identifies features within the acoustical signature of an inertia friction weld that are indicative of the process's ability to produce a quality bond; (2) provides a real-time response with minimal hardware requirements; and (3) tolerates noisy and ill-defined data.

The results produced by this example may be extended into these other areas: (1) compare and contrast the non-contact sensing capabilities of this sensor with a piezoelectric transducer as described in Wang, K., Reif, G., and Oh, S., "In-Process Quality Detection of Friction Welds Using Acoustic Emission Techniques," *Welding Journal*, 61, 312s–316s (September 1982), the entire contents of which are hereby incorporated by reference; (2) generate a larger experimental matrix to include contamination conditions (e g., fingerprints) to freshly machined surfaces; (3) determine the directional characteristics of the sensing ring, (4) investigate other feature extraction methods, such as, wavelets and spectograms; and (5) analyze the data with other neural network techniques, such as, an adaptive probabilistic neural network.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for determining the quality of an examined weld joint comprising the following steps:

(a) providing acoustic data from said examined weld joint; and (b) performing neural network operations on said acoustical data to determine the quality of said examined weld joint, wherein said examined weld joint is produced by a friction weld process.

2. The method of claim 1, wherein step (b) comprises determining whether said examined weld joint is acceptable or conditional.

3. The method of claim 2, wherein step (b) further comprises determining whether said examined weld is acceptable or unacceptable, wherein said examined weld joint is acceptable, conditional or unacceptable.

4. The method of claim 1, wherein step (b) comprises determining whether said examined weld joint is acceptable or unacceptable.

5. The method of claim 1, wherein said neural network is trained by a method comprising the following steps:

inputting acoustical data from at least one test weld joint;

inputting observable data from said at least one test weld joint; and training said neural network based on said acoustical data and said observable data to form a trained neural network so that said trained neural network is capable of determining the quality of said examined weld joint based on acoustical data from said examined weld joint.

6. The method of claim 5, wherein said neural network is further trained by a method comprising the following steps:

providing acoustical data from a first examined weld joint; and training said trained neural network based on said acoustical data to form an adapted trained neural network so that said adapted trained neural network is capable of determining the quality of an second examined weld joint based on acoustical data from said second examined weld joint.

7. The method of claim 1, wherein said method is performed in real-time while said examined weld joint is formed from said friction weld process.

8. The method of claim 1, wherein said acoustical data comprises samples of an acoustical signature from said examined weld joint sensed by at least one acoustical sensor.

9. The method of claim 8, wherein said acoustical data is based on frequency information, and wherein said frequency information is obtained by using a discrete Fourier transform on said acoustical signature.

10. The method of claim 1, wherein said acoustical data comprises samples of an acoustical signature from said examined weld joint using at least two acoustical sensors.

11. The method of claim 10, wherein said acoustical data is based on frequency information and phase information, wherein said frequency information obtained using a discrete Fourier transform on said acoustical signature, and wherein said phase information is based on a time-domain relationship between said at least two acoustical sensors.

12. The method of claim 1, wherein step (b) is implemented in a computer.

13. The method of claim 1, wherein said neural network is a probabilistic neural network (PNN).

14. A method for training a neural network comprising the following steps:

providing acoustical data from at least one test weld joint;

providing observable data from said at least one test weld joint; and training said neural network based on said acoustical data and said observable data to form a trained neural network so that said trained neural network is capable of determining the quality of an examined weld joint based on acoustical data from said examined weld joint.

15. The method of claim 14, wherein said neural network is capable of determining whether said examined weld joint is acceptable or conditional.

16. The method of claim 14, wherein said neural network is capable of determining whether said examined weld joint is acceptable or unacceptable.

* * * * *